(12) United States Patent
Loeb et al.

(10) Patent No.: US 6,286,512 B1
(45) Date of Patent: Sep. 11, 2001

(54) ELECTROSURGICAL DEVICE AND PROCEDURE FOR FORMING A CHANNEL WITHIN TISSUE

(75) Inventors: Marvin P. Loeb, Huntington Beach; L. Dean Crawford, Irvine; Samuel M. Shaolian, Laguna Niguel, all of CA (US)

(73) Assignee: Cardiodyne, Inc., Irvine, CA (US)

( * ) Notice: Subject to any disclaimer, the term of this patent is extended or adjusted under 35 U.S.C. 154(b) by 0 days.

(21) Appl. No.: 09/000,987

(22) Filed: Dec. 30, 1997

(51) Int. Cl.[7] .................................................. A61B 19/00
(52) U.S. Cl. ............................................. 128/898; 606/41
(58) Field of Search .............................. 606/41, 45, 167, 606/46–48, 170; 607/115, 119, 122, 123; 604/22; 600/564; 128/898

(56) References Cited

U.S. PATENT DOCUMENTS

| | | | |
|---|---|---|---|
| 5,125,926 | * 6/1992 | Rudko et al. | 606/19 |
| 5,380,316 | 1/1995 | Aita et al. | 606/7 |
| 5,389,096 | 2/1995 | Aita et al. | 606/2 |
| 5,893,848 | * 4/1999 | Negus et al. | 606/41 |
| 5,899,915 | * 5/1999 | Saadat | 606/170 |

OTHER PUBLICATIONS

U.S. Patent application Ser. No. 08/790,546, filed Jan. 30, 1997, to Loeb et al.

Mirhoseini et al., Revascularization of the Heart by Laser, Journal of Microsurgery, Jun. 1981.

* cited by examiner

Primary Examiner—Linda C. M. Dvorak
Assistant Examiner—R. Kearney
(74) Attorney, Agent, or Firm—Olson & Hierl, Ltd.

(57) ABSTRACT

A surgical device is provided for forming a channel through or into tissue utilizing radio-frequency electrical energy. The device includes a cannula having an open bore. Mounted within the bore is an insulated mono-polar electrical lead, the distal end of which is not insulated, for forming the channel by mechanically advancing through the tissue and emitting radio-frequency energy. Alternatively, the device can have bipolar electrical leads.

21 Claims, 21 Drawing Sheets

300 msec $\leq \Delta T_2 \leq$ 450 msec (TOTAL TREATMENT TIME/CHANNEL)

$\Delta T_1 \leq$ 150 msec (SHIFT FROM R WAVE)

$\Delta T_4 = \Delta T_4 = \dfrac{\Delta T_2 - \Delta T_3}{2}$ = 45-50 msec (NO RF ENERGY APPLIED)
$\phantom{\Delta T_4 =}$IN $\phantom{==}$OUT

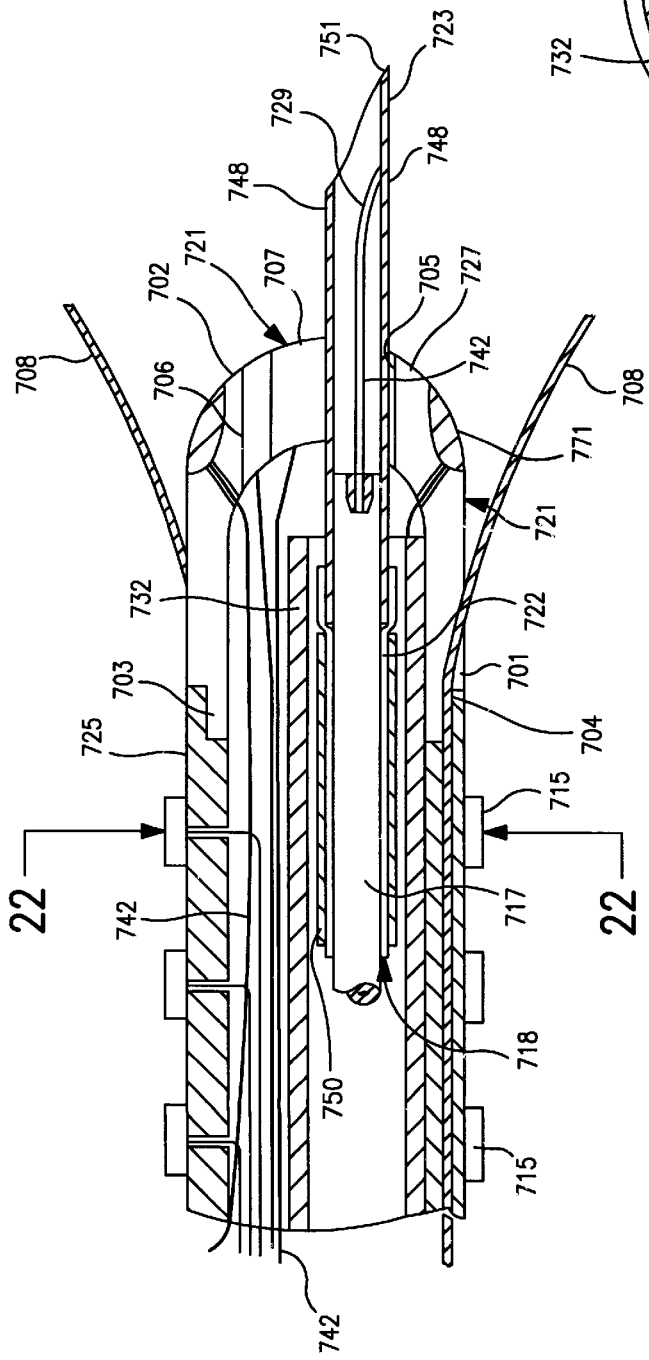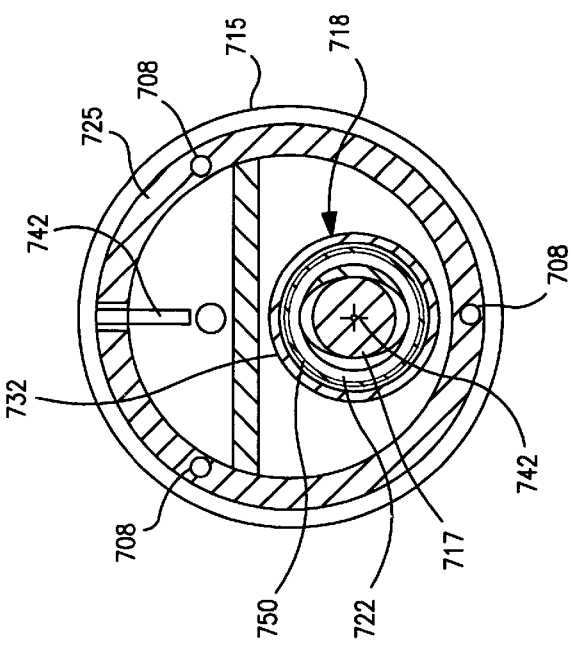

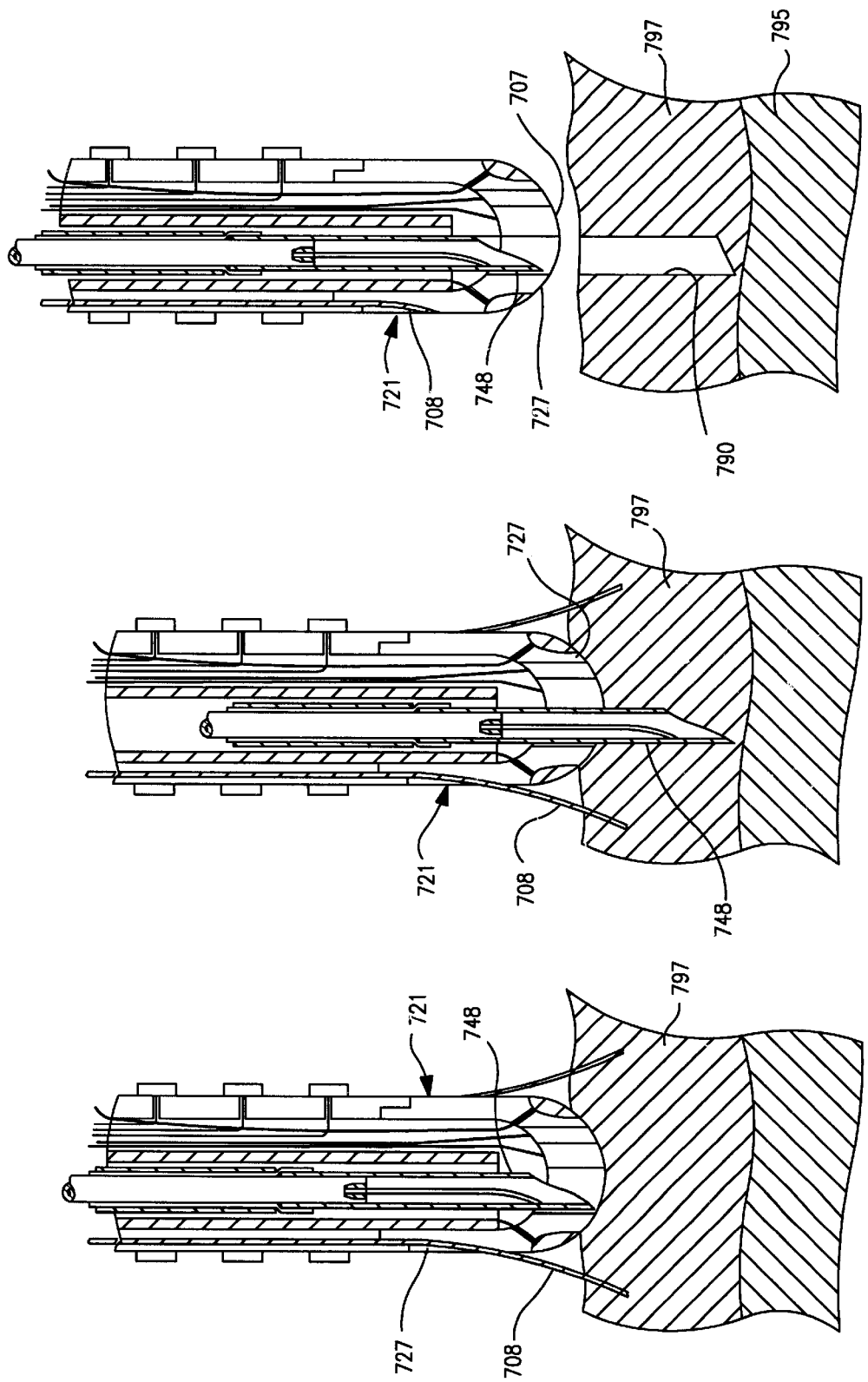

ELECTROSURGICAL DEVICE AND PROCEDURE FOR FORMING A CHANNEL WITHIN TISSUE

FIELD OF THE INVENTION

The present invention relates to surgical devices and procedures for the delivery of electrical energy to form a channel within tissue, and in particular to a device and procedure which forms a channel by emitting energy at radio-frequencies directly onto the tissue.

BACKGROUND OF THE INVENTION

A human heart receives its blood supply from the coronary arteries, which branch out and around the heart muscle. Conversely, in a reptile, little or no arterial supply of blood is provided to the heart. Instead, the blood supply is mainly delivered into the heart muscle from the inside surface of the heart chamber.

Modifying a human heart to imitate the blood delivery method of a reptile heart is currently being used as an alternative or adjunct to both coronary artery bypass graft surgery and coronary balloon angioplasty. Normally, a person can only undergo coronary bypass surgery twice, since the risks will begin to outweigh the benefits after that point. Thus, in the past, a patient who has already had two coronary bypass surgeries was left with no recourse. Others have failed repeated coronary balloon angioplasties, and many persons are not suitable candidates for coronary bypass surgery or coronary balloon angioplasty. These persons likewise are left with no treatment options.

Early attempts to imitate the reptilian condition in mammals, known as transmyocardial revascularization (TMR), consisted of producing tiny channels in mammalian and human hearts with needles or pre-heated wires. These methods met with limited success since, although the channels closed by clotting at the outside surface of the heart due to exposure to air, and did allow for some internal blood delivery, the channels soon healed over entirely and failed to continue to enhance the blood supply. Early attempts were also made to graft a blood vessel from the aorta directly into the heart muscle to provide an internal source of blood. While some benefits were seen, the surgery was technically demanding and the procedure was eclipsed by the introduction of coronary artery bypass graft surgery.

To overcome these problems, Mahmood Mirhoseini and Mary M. Cayton attempted transmyocardial revascularization by using a $CO_2$ laser to make the channels. Mirhoseini M., Cayton M. M., *Revascularization of the Heart by Laser*, J Microsurg 2:253, June, 1981. The laser forms each channel by vaporizing a passageway completely through the wall of the heart. The relatively clean channel formed by the laser energy prevents the channel from healing over, and the channel either closes by clotting at the heart's outer surface, due to exposure to air, or manual pressure can be applied until bleeding from the channel ceases. In some cases, a suture is required to close the channel. However, if bleeding cannot be stopped, or if bleeding resumes at a later time, after the patient is no longer in surgery, the patient may require emergency surgery or may die.

Generally, it is desired that the channels be made primarily within the heart's inner surface (endocardium) since the endocardium has a greater need of an alternative supply of blood than the heart's outer surface (epicardium). It would be desirable not to create too large a channel through the epicardium because the channel must clot and/or heal at the heart's surface to prevent copious blood loss due to the forceful pumping action of the heart. It would be desirable to produce a channel which is very small in the epicardium, so that clotting can easily close the channel at the heart's outer surface, as well as a channel which is widest at the point the channel exits the inner surface of the heart chamber, thus admitting a larger volume of blood and being less susceptible to clotting or healing.

The present invention satisfies these objectives by providing an improved device and procedure that employs radio-frequency electrical energy to form a channel.

SUMMARY OF THE INVENTION

The present invention provides a device and procedure to create a channel into the endocardium and in fluid communication with the heart chamber. The channel is formed by delivering radio-frequency electrical energy directly onto a selected tissue site where a channel is desired.

The device embodying the present invention is especially suitable for use in medical applications for the delivery of radio-frequency energy at a controlled rate in a uniform manner, so the depth of coagulation surrounding the channel can be controlled as desired. In addition, the present device allows formation of uniformly or otherwise desirably shaped channels in a periodically moving structure such as a human heart.

A surgical device embodying the present invention includes a housing, a cannula mounted to the housing, and an electrically conductive lead assembly received within a bore that passes through the cannula. An actuator is operably coupled to the housing for advancing the lead assembly into tissue. The lead is energized by a suitable radio-frequency electrical energy source to form the channel in a desired tissue layer.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same.

FIG. 21 is an enlarged longitudinal fragmentary partially cross-sectional view of the distal end portion of the catheter of FIG. 20 having a lead assembly and engagement wires extending therefrom;

FIG. 22 is a cross-sectional end view of the catheter along plane 22—22 of FIG. 21;

FIG. 23A is a fragmentary partially cross-sectional view of the distal end portion of the catheter of FIG. 21 pressed against the inner surface of a heart with engagement wires anchoring the catheter thereto;

FIG. 23B is similar to FIG. 23A, except that the lead assembly has been advanced into the heart while the end portion of the catheter remains pressed against the heart inner surface; and FIG. 23C is similar to FIG. 23A, except that the lead assembly has been withdrawn from the heart, exposing the channel formed therein, and the lead assembly and the engagement wires have been retracted back into the catheter.

DISCLOSURE OF THE PREFERRED EMBODIMENTS

The present invention provides a surgical device for forming a channel by employing radio-frequency electrical energy, emitted directly onto a tissue layer, to create a channel. The device includes an electrical lead assembly that is advanced within the tissue layer and facilitates the emission of radio-frequency energy thereon.

While this invention is susceptible of embodiments in many different forms, this specification and the accompanying drawings disclose only some specific forms as examples of the invention. The invention is not intended to be limited to the embodiments so described, however. The scope of the invention is pointed out in the appended claims.

Figure 1:
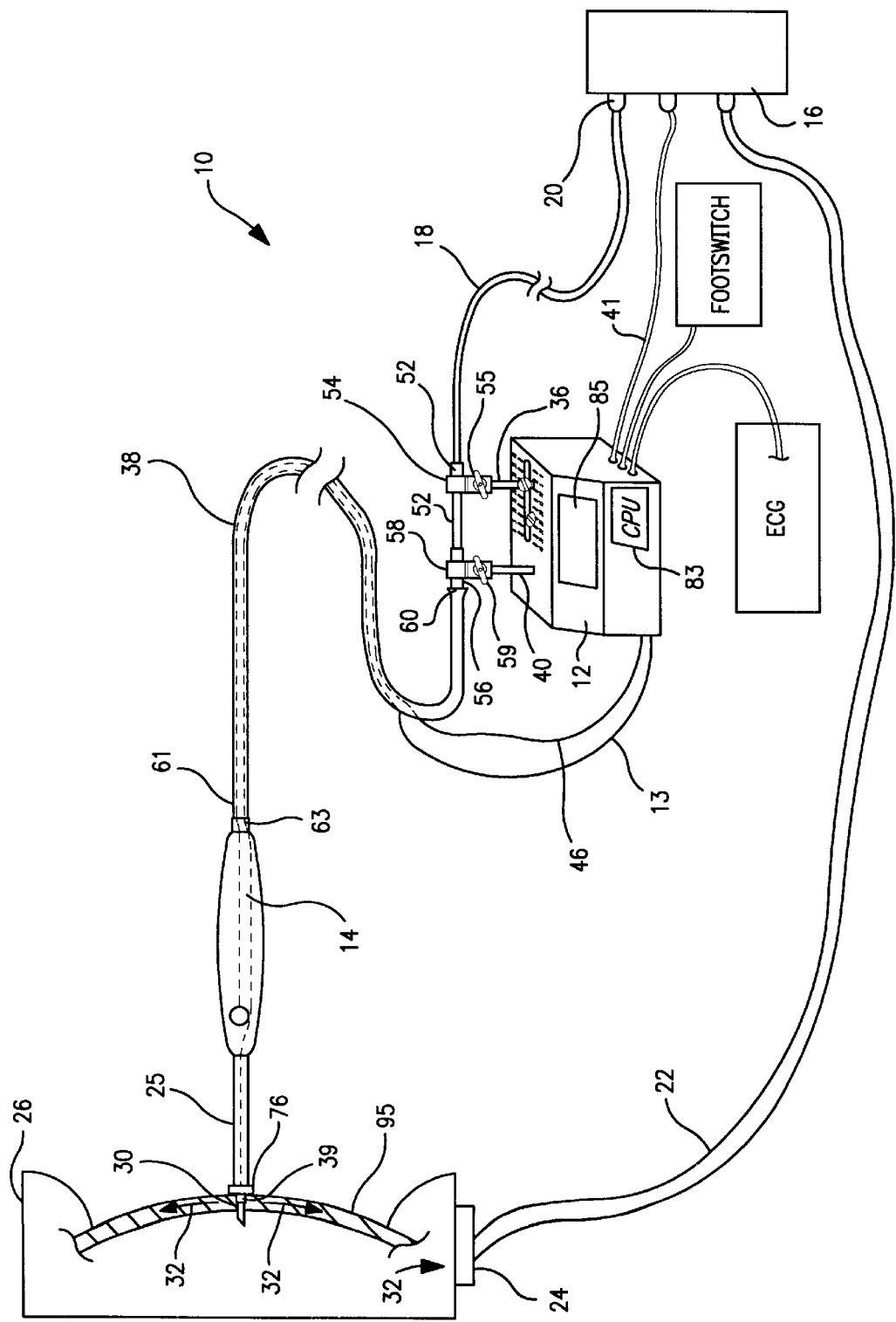
FIG. 1 is a perspective view of an embodiment of the present invention having an actuator for advancing into and withdrawing from the heart wall a lead assembly from the cannula of an attached handpiece.

Referring to FIG. 1, a perspective view of a device 10 in accordance with the present invention is shown. The device 10 has an external mechanical actuator 12 that is operably connected to a housing or handpiece 14, a radio-frequency (RF) energy source 16, and a conventional electrocardiograph (ECG). The RF source 16 is of a conventional type providing about 50 to 300 watts with impedance matching for a 50 ohm load. The frequency of the RF electrical energy provided by source 16 preferably is in a range that is greater than about 10 kHz but less than about $10^{12}$ Hz.

The output terminal of the RF source 16 is operably connected to electrical lead assembly 18 by connector 20. For mono-polar operation, the return terminal of the RF source 16 is connected, via return lead 22, to a conventional return electrode 24 that is externally attached to patient 26. Alternatively, as discussed in detail further herein, the return terminal can be connected to the electrical lead assembly 18 in a bi-polar configuration.

In operation, a rigid collar or cannula 25 extending from the handpiece 14 is pressed against the outer surface of a heart 95. This activates a switch within handpiece 14 to enable the control unit 83 within actuator 12 to track the next "r" wave of a patient's ECG. The actuator 12 then advances the lead assembly 18 into the heart wall on the next recognizable "r" wave. After penetrating the heart wall by a preselected distance, RF energy is emitted as the lead assembly 18 continues to advance through the heart 95 and into the chamber. The emission of RF energy is then ceased and the lead assembly is withdrawn from the epicardium. Optionally, RF energy can continue to be emitted as the lead assembly passes back through the endocardium to the point where RF energy was initiated.

During emission of RF energy with a mono-polar lead assembly, the RF energy shown as current 32 in FIG. 1 flows from the heart 95, through the tissue of the patient 26 and into the return electrode 24 where it travels back to the RF source 16. Alternatively, with a bi-polar lead assembly, as described in detail further herein, a return path is provided for the RF energy wherein a substantial amount of the current 32 used in the channel forming process does not pass from the heart to other tissue of the patient 26.

The lead assembly 18 is attached to drive arm 36 of actuator 12, extends through a flexible interconnecting cannula 38, and into handpiece 14. The lead 18 is allowed to slide within cannula 38 with the proximal end of the cannula attached to fixed arm 40 of actuator 12 and the distal end of the cannula attached to handpiece 14 to operably connect the actuator and the handpiece together.

Figure 2:
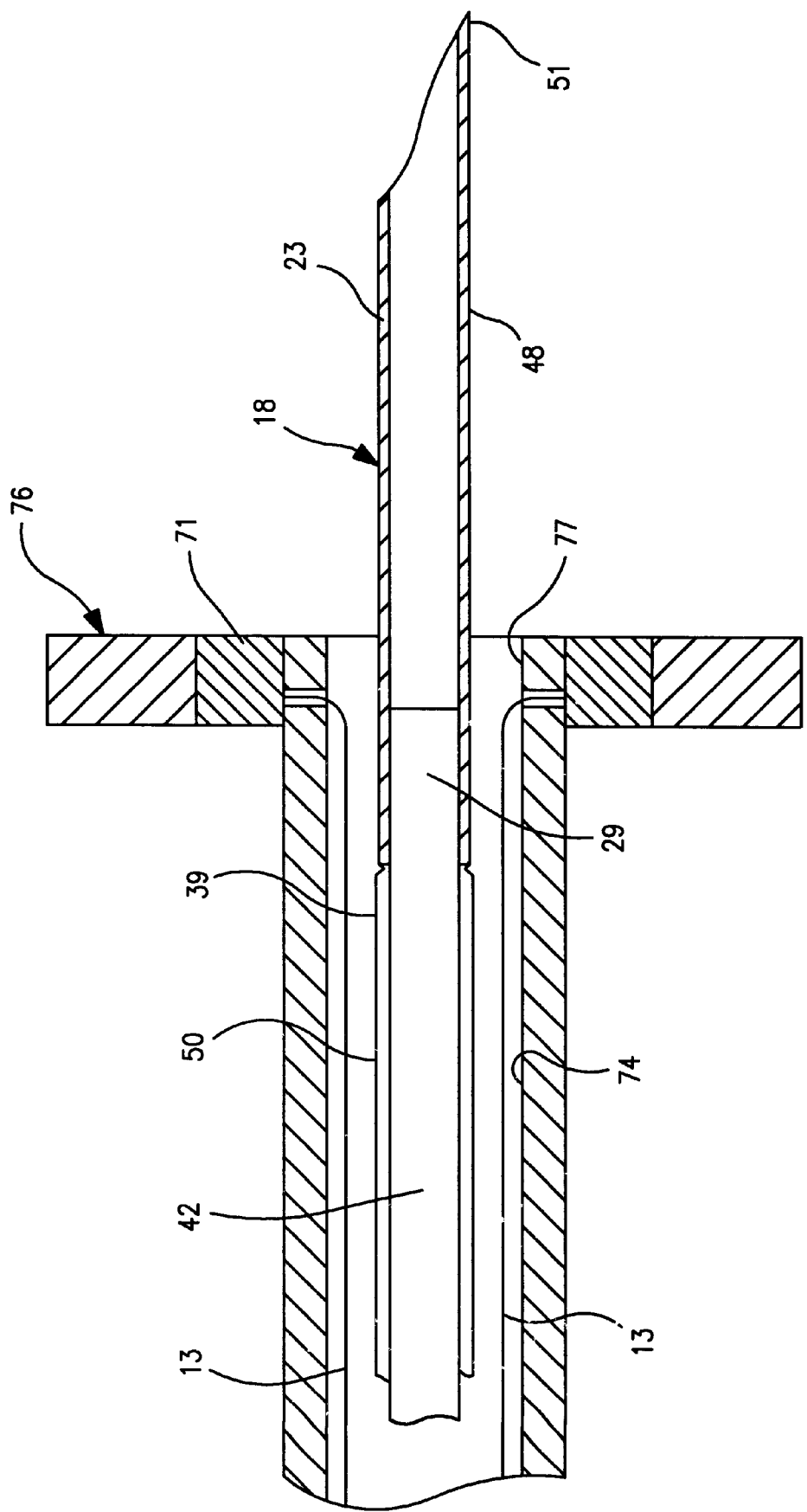
FIG. 2 is an enlarged cross-sectional view of an embodiment of the lead assembly of FIG. 1 projecting from the cannula for mono-polar RF energy delivery.

FIG. 2 is an enlarged cross-sectional view of an embodiment of the lead assembly of FIG. 1 projecting from rigid cannula 25 for mono-polar RF energy delivery. The mono-polar electrical lead assembly 18 includes a length of electrically conductive wire 42 made of a suitable conductive material such as copper and having a distal end 29. The wire 42 is surrounded by an electrically insulating layer 50 that can be a plastic material or a composite having the appropriate dielectric properties. The insulation layer 50 is generally tubular in shape and covers the wire 42 to a terminal end 39 proximate an exposed portion of the wire 42 that linearly projects from the insulation. Receiving and attached to the distal end of the wire 42 proximate to insulation 50 is a electrically conductive needle 23 that provides a generally cylindrical mono-polar electrode 48 with a tip 51 that can be pointed, beveled, blunted, or any other shape that is well known in the art.

In an alternative embodiment, the lead assembly can be provided with electromagnetic shielding (not shown) between the insulation layer 50 and the wire 42. The electromagnetic shielding surrounds the wire 42 in an arrangement similar to a coaxial cable. The shielding can consists of conductive material, such as braided copper wires. The shielding is coupled to an electrical ground or the like that is proximate to, or provided by, the RF generator 16. Accordingly, the shielding provides for substantially preventing the radiation of electromagnetic energy from that portion of the lead assembly 18 outfitted with the shielding. Preferably, the electromagnetic shielding extends proximate to the needle 23, but is not in electrical contact therewith.

Figure 3:
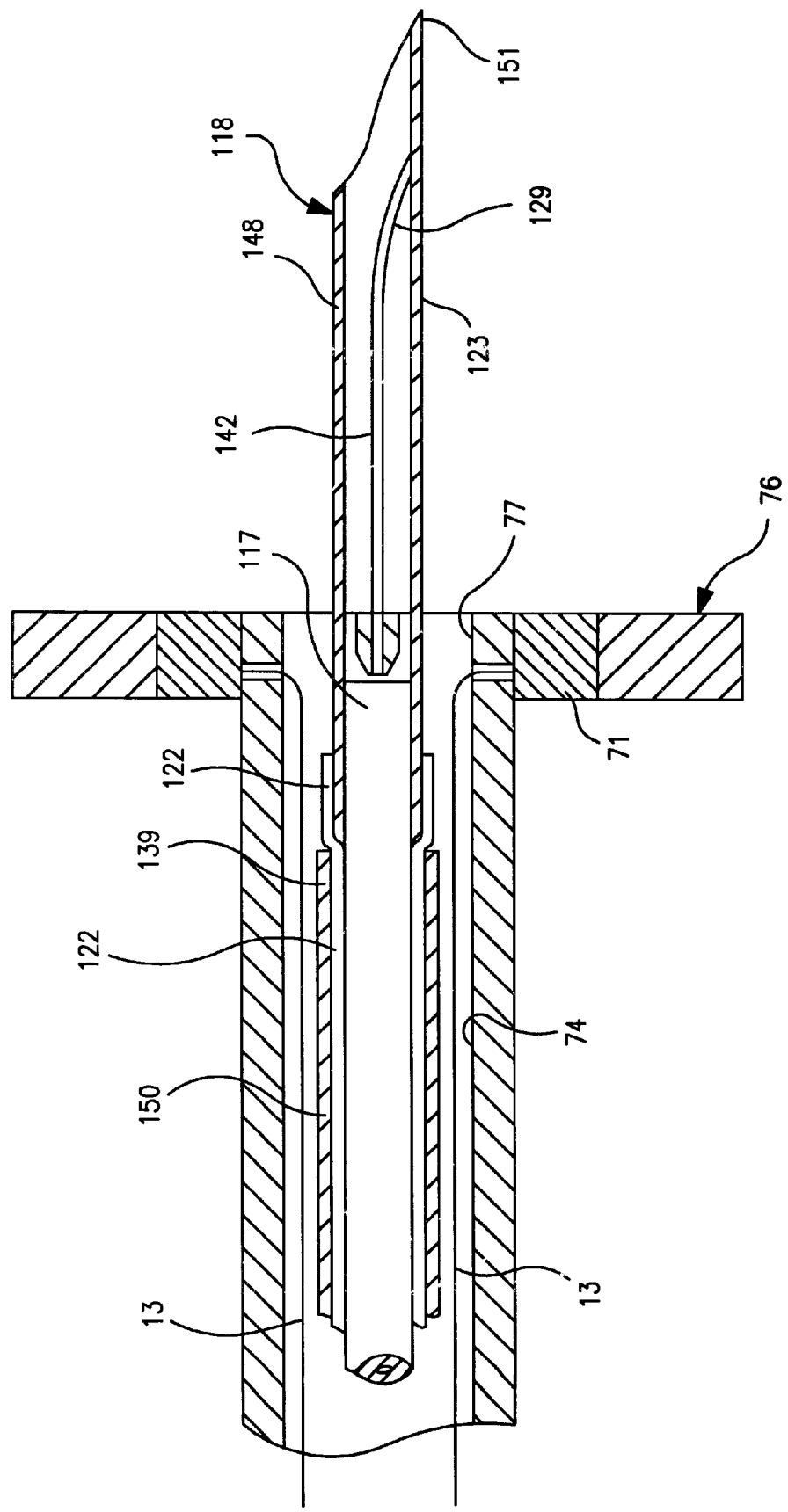
FIG. 3 is an enlarged cross-sectional view of an alternative embodiment of the lead assembly of FIG. 1 extending from the cannula for bi-polar RF energy delivery.

Turning to FIG. 3, an enlarged cross-sectional view is depicted of an alternative embodiment of a lead assembly extending from cannula 25 for bipolar RF energy delivery. The lead assembly 118 is like that shown in FIG. 2 except that it is bipolar and thus includes both conductive center wire 142 and return lead 122 in an arrangement similar to that of a coaxial cable. Correspondingly, where appropriate, the last two digits in the 100 series of numerals depicted in FIG. 3 are connected to elements which have a similar function and/or structure as those described with regard to FIG. 2.

The center wire 142 of the lead assembly 118 is coupled to the RF output of the electrosurgical generator 16 of FIG. 1. The distal end 129 of the center wire 142 is attached to an electrically conductive needle 123 that provides a generally cylindrical bipolar electrode or load 148 with a tip 151 that is pointed, but can have any other desired shape such as, for example, being beveled, blunted, or having a sharp-point for piercing the wall of a cavity like that of a trocar (i.e., trocar shaped).

The center wire 142 is surrounded by an inner electrically insulating layer 117 which is generally tubular in shape and substantially covers the outer surface of the wire length except for the distal end 129 longitudinally projecting therefrom.

Attached to the outer surface of the inner insulating layer 117 is return lead 122 that surrounds the insulating layer except for a distal portion proximate to, and extending within, electrode 148. The return lead 122 is generally tubular in shape and is made of conductive material such as metal or metal alloy. The return lead 122 may, for example, consists of a single solid conductor or a plurality of braided conductor strands. Desirably, the distal end of the return lead 122 receives, and is attached to, a portion of the outer surface of the electrode 148 such that an electrically conductive path is provided therebetween.

Along the length of the return lead 122, the center wire 142 is preferably in longitudinal coaxial alignment with the return lead 122. Further, the inner insulating layer 117 is situated between the center wire 142 and the return lead 122 such that they are electrically isolated from each other. Surrounding the outer surface of the return lead 122 along its length, except for the portion receiving the needle 123, is an outer electrically insulating layer 150.

Figure 4:
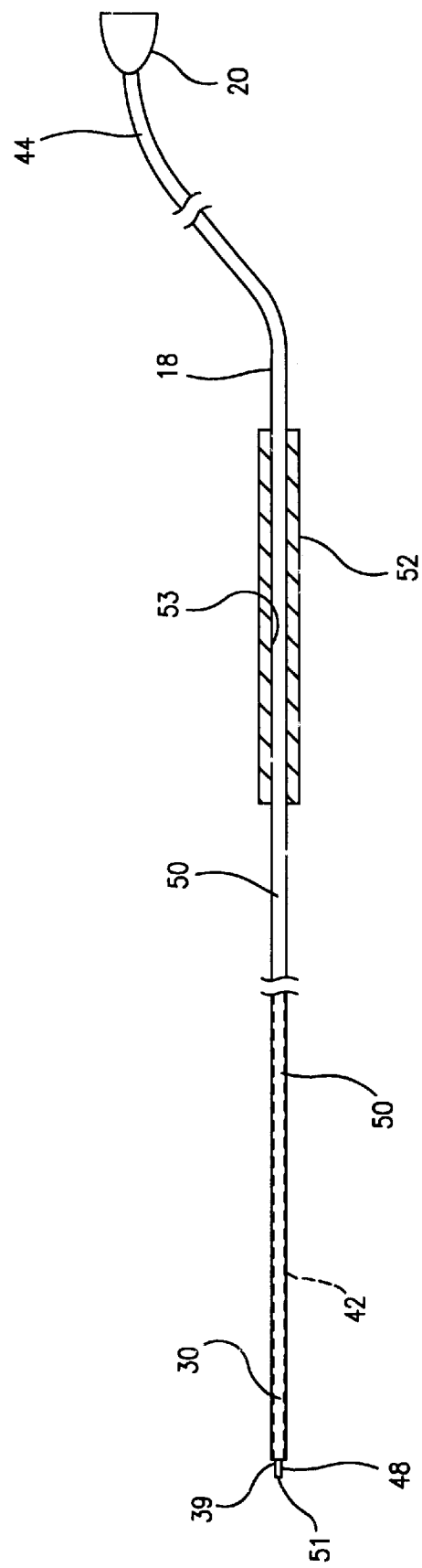
FIG. 4 is a partial cross-sectional perspective view of the lead assembly of FIGS. 1 and 2 removed from the handpiece and extending through an attached support tube.

Referring to FIG. 4, electrical lead assembly 18 includes a proximal end 44 and a distal end 30. As stated above, the proximal end 44 is coupled to connector 20. Further, the distal end 30 provides a generally cylindrical electrode 48 with a tip 51 that can be pointed, beveled, blunted, trocar shaped, or any other shape as well known in the electrosurgery art.

Attached to the outer non-conductive surface of lead assembly 18 is a support tube 52 for providing added rigidity and preventing the lead from being damaged by the force exerted while the lead assembly is advanced by drive arm 36 of actuator 12. The support tube 52 is preferably made of plastic and has a longitudinal open bore 53 for receiving the lead assembly 18 which extends through the bore. The lead 18 is secured to the support tube 52 by adhesive or the like.

Returning to FIG. 1, the outer surface of support tube 52 is removably grasped by clamp 54 of drive arm 36. The clamp 54 releases and secures the support tube 52 by loosing and tightening, respectively, clamp adjustment handscrew 55.

Figure 5:
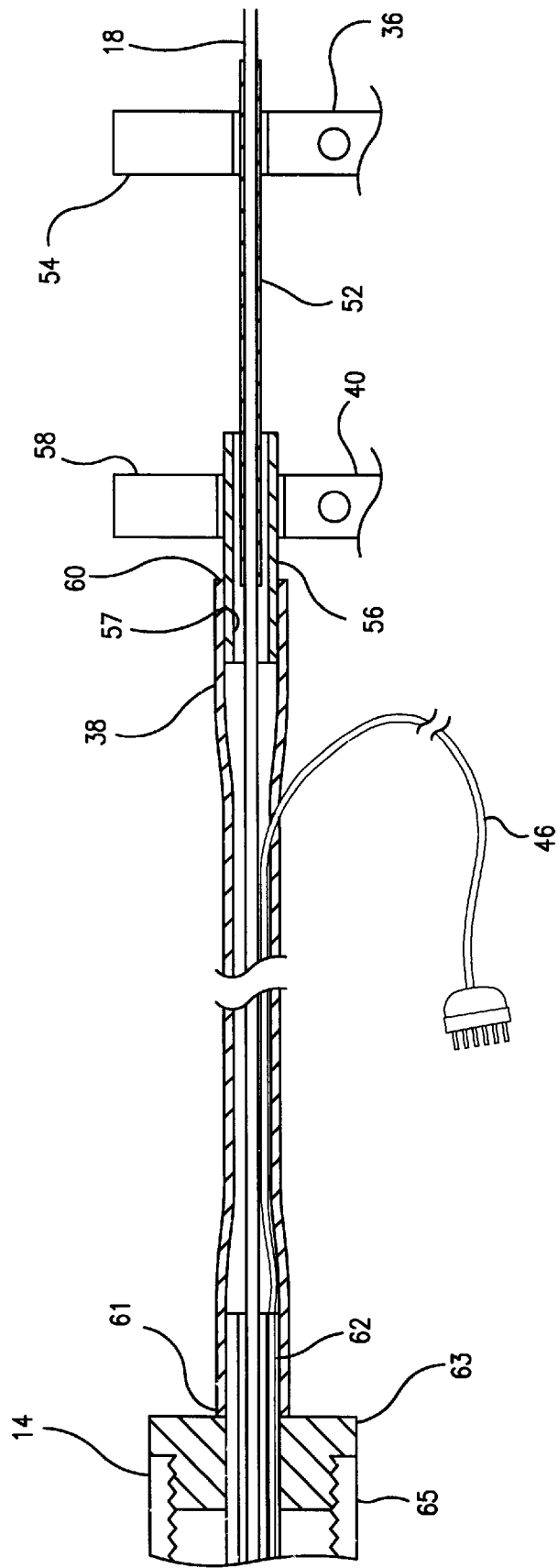
FIG. 5 is a cross-sectional view of the lead assembly of FIGS. 1 and 2 passing through a flexible interconnecting cannula and into the handpiece.

FIG. 5 depicts the support tube 52 and attached lead assembly 18 passing through a bushing 56 removably mounted onto the fixed arm 40 of the actuator 12. The bushing 56 may be made of metal or plastic and has a longitudinal open bore 57 for slidably receiving support tube 52 and lead assembly 18. The inner diameter of the bushing bore 57 is greater than the outer diameter of the support tube 52 to allow the support tube to freely slide within the bushing 56.

The bushing 56 is removably grasped by clamp 58 of fixed arm 40. The clamp 58 releases and securely holds the tube by loosing and tightening, respectively, clamp adjustment handscrew 59.

One terminal end 60 of interconnecting cannula 38 is attached to bushing 56 by partially inserting the bushing into the cannula. Adhesive or the like may also be used in securing the cannula 38 to the bushing 56.

The other terminal end 61 of the interconnecting cannula 38 is attached to a nipple 62 extending from plug 63 of handpiece 14. The cannula 38 is fitted over the outer surface of the nipple 62 and may be secured to the nipple by adhesive or the like. Signal wires 46 extend from the switch 80 within the handpiece 14, and form other electrical elements, if desired, such as buttons, indicator light emitting diodes (LEDs) and sensors are operably connected to the microcontroller 83 of actuator system 12.

Figure 6:
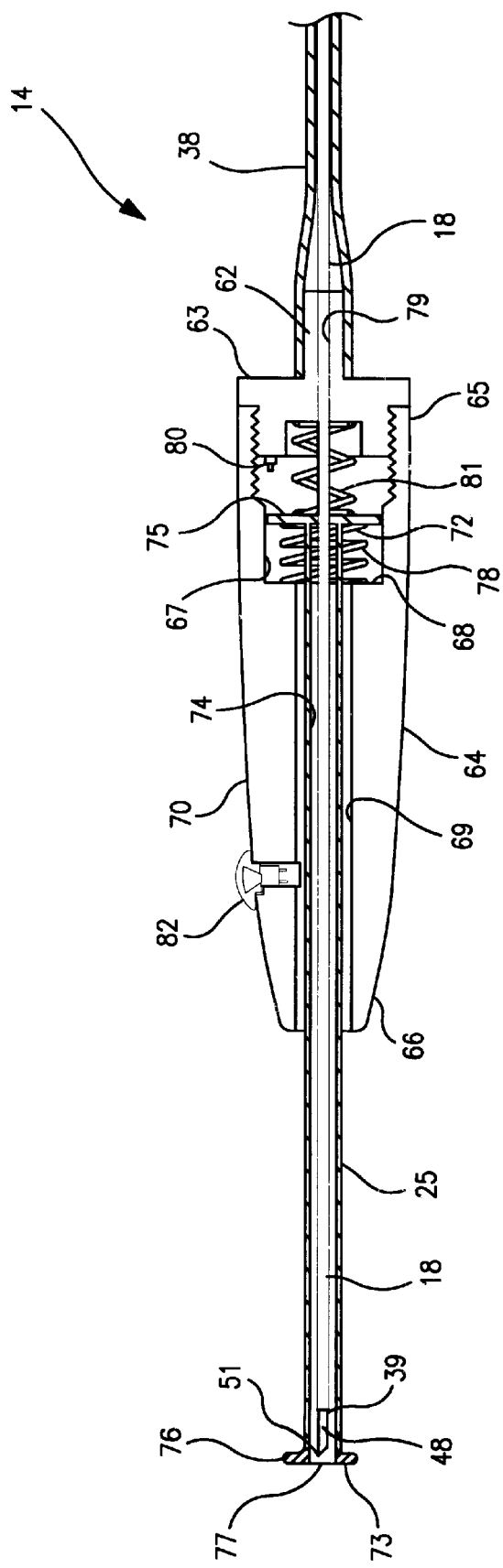
FIG. 6 is a partial cross-sectional view of an embodiment of the handpiece of FIG. 1.

FIG. 6 provides a partial cross-sectional view of the handpiece 14. The handpiece 14 includes a generally cylindrical housing 64 having a first end 65 and a tapered second end 66 with an elongated cavity 67 extending therebetween.

Defined within the housing cavity 67 is a shoulder 68. The shoulder 68 is ring shaped and results in the housing cavity 67 having a cylindrical longitudinal portion or passage 69 that is in communication with the outside 70 of the housing 64 at the second end 66.

Slidably mounted within the housing cavity 67 and extending from the second end 66 of the handpiece 14 is rigid hollow tubular cannula or guide 25. The rigid cannula 25 is generally cylindrical in shape with an inner end 72, an outer end 73, and an open bore 74 extending therebetween.

The inner end 72 of the cannula 25 extends past shoulder 68 and has a radially outwardly extending retaining ring 75 with a larger outer diameter than the inner diameter of cavity passage 69. Likewise, the outer end 73 of the cannula 25 protrudes from passage 69 and has a rounded flange 76 extending around its periphery. The flange 76 results in the outer end 73 of the cannula 25 having a flat disk shaped surface with the aperture 77 to bore 74 being located in the center.

Referring back to FIGS. 2 and 3, in an embodiment, the flange 76 can include a disk shaped ultrasound transducer 71 having leads 13 extending within the cannula bore 74 to control unit 83 and/or a display unit. Preferably, the disk shaped ultrasound transducer 71 surrounds, and is proximate to, the aperture 77 of the cannula bore 74.

As shown in FIG. 6, located between retaining ring 75 and shoulder 68 is coiled spring 78 which wraps around the outer surface of the cannula 25. The coiled spring 78 retractably biases the cannula 25 towards the first end 65 of the housing 64.

Threadingly mounted onto the first end 65 of the housing 64 is plug 63 having an open bore 79 in communication with the housing cavity 67 and extending through nipple 62. Extending through plug bore 79 and into the cannula bore 74 is lead assembly 18.

Also mounted onto the plug 63 is an electrical switch 80 which faces towards retaining ring 75 within housing cavity 67. The switch 80 provides a means for detecting when the cannula 25 has been pushed a fixed distance within the housing cavity 67. correspondingly, the switch 80 is activated only when the retaining ring 75 of the cannula 25 abuts against the switch.

Resiliently biased against retaining ring 75 and plug 63 is coiled spring 81 which forward biases the cannula 25 away from the first end 65 of the housing 64.

Attached to the housing 64 is an LED 82 for indicating that the ring 75 of cannula 25 has contacted microswitch 80, or alternatively, indicating that the device is "armed", or both. The LED 64 is operably connected by conventional means such as wire leads within wire harness 46 (FIG. 5) to the control unit 83 within the actuator 12.

Figure 7:
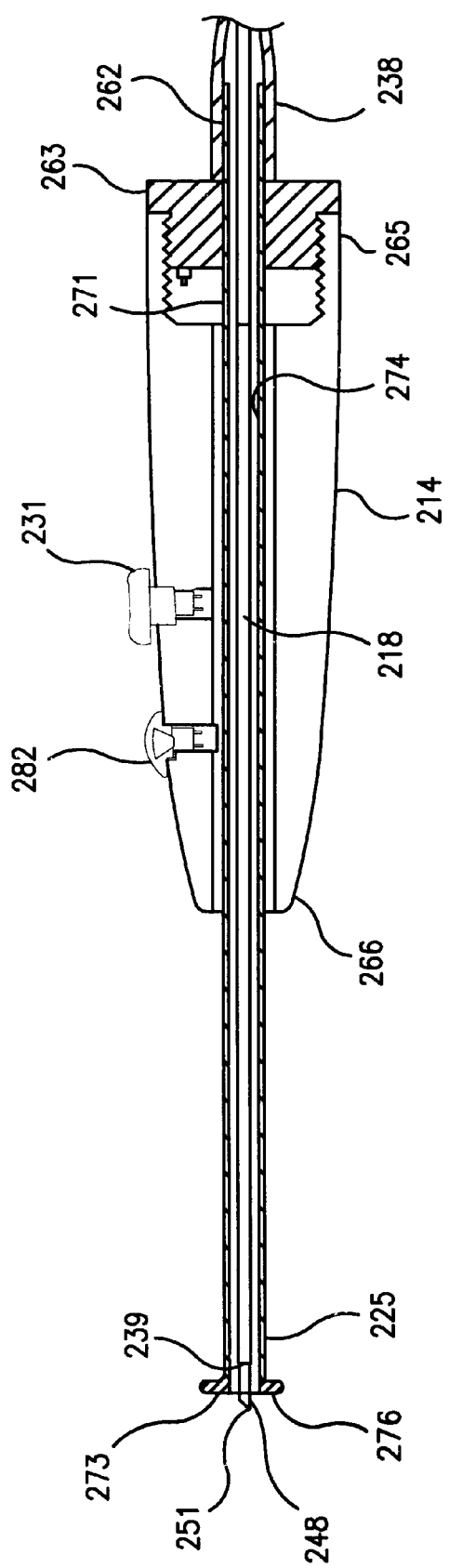
FIG. 7 is a partial cross-sectional view of another embodiment of the handpiece of FIG. 1 with the cannula fixedly attached to the handpiece.

FIG. 7 depicts a cross-sectional view of another handpiece in accordance with the present invention. The handpiece 214 is similar to that shown in FIG. 6 except that the rigid cannula 225 is securely mounted to the handpiece housing and an activating button 231 is provided. Correspondingly, where appropriate, the last two digits in the 200 series of numerals depicted in FIG. 7 are connected to elements which have the same function and/or structure as those described with regard to FIGS. 1–6.

In FIG. 7, cannula 225 is secured to plug 263 and extends from both the first end 265 and the second end 266 of the handpiece 214. Attached to the portion 262 of the rigid cannula 225 that extends from the handpiece first end 265 is flexible interconnecting tube or cannula 238.

The lead 218 within the interconnecting cannula 238 passes into the rigid cannula's bore 274. The pointed tip 251 of the electrode 248 is positioned proximate to, and projecting from, the rigid cannula's second end 273.

Activating button 231 is mounted on the outside of the handpiece 214 and is operably connected to the control unit 83 of the actuator 12. The button 231 is preferably depressed by a surgeon when the electrode 248 partially extends into an arrested heart and the second end 273 of the cannula 225 abuts against the heart. Depressing the button 231 commands the device to begin forming a channel in the heart as described above with regard to FIGS. 1–10.

In an alternative embodiment wherein the heart is beating, depressing the button 231 enables the control unit 83 within the actuator 12 to advance the lead assembly 218 into the heart wall after an appropriate period of time following the next recognizable "r" wave, as it is preferable to create the channel between the end of the "t" wave and the beginning of the "p" wave of the patent's ECG, during diastole, when the heart's electrical activity is minimal. Further, in yet another embodiment, depressing the button will "arm" the device 210, but the actuator 12 will not advance the lead until footswitch or the like is depressed and the next recognizable "r" wave is detected.

Referring to FIGS. 5 and 7, by adjusting the position of the lead within clamp 54 of activator arm 36, the distal tip 251 of the lead may be extended 1 to 6 millimeters, preferably about 3 to 4 millimeters, distally from flange 276 of cannula 225. In this embodiment, when handpiece flange 276 is pressed against the heart, electrode 248 penetrates into the epicardium. When button 231 is depressed, if the heart is arrested then the channel making progress proceeds, however, if the heart is beating then on the next recognizable "r" wave, after an appropriate delay time, the lead 218 advances through the endocardium and into the heart chamber wherein RF energy is emitted from the electrode 248 to burn a channel in the endocardium. The RF energy transmission is later terminated and the electrode 248 is retracted to its original position. Cannula 225 of handpiece 214 is then manually withdrawn from the heart.

Figure 8:
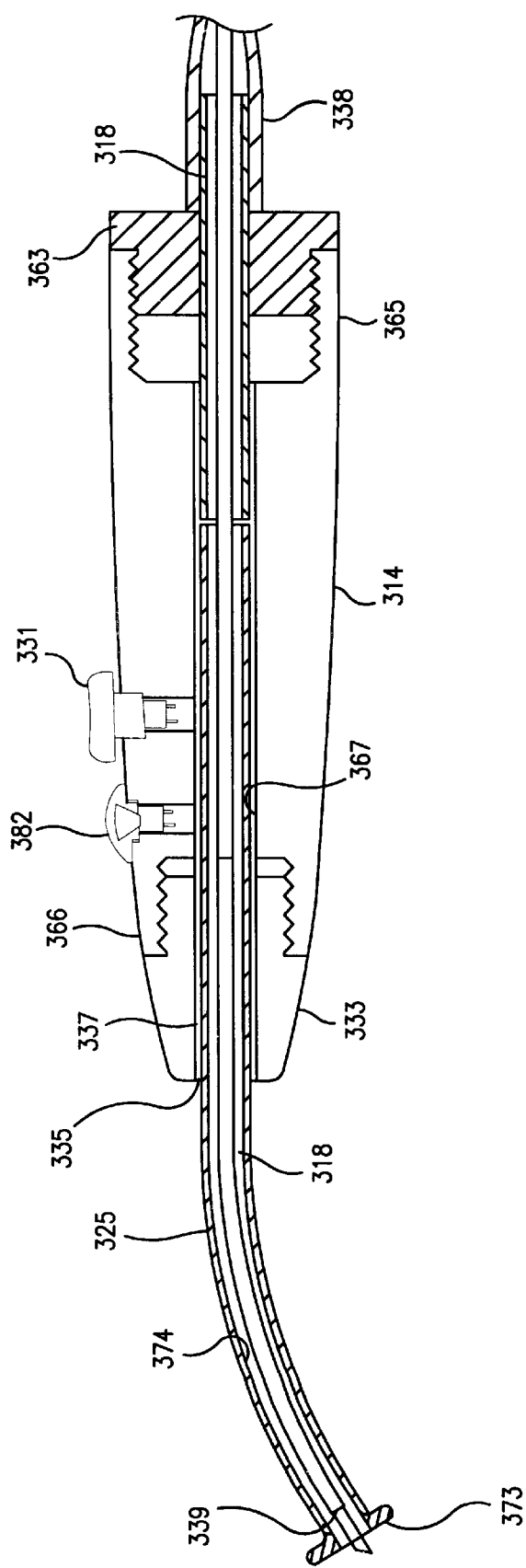
FIGS. 8 and 9 are partial cross-sectional views of alternate embodiments of the handpiece of FIG. 7 with the cannula being arched and detachable from the handpiece.

FIG. 8 shows an alternate embodiment of the handpiece shown in FIG. 7, except that the cannula is detachably secured to the handpiece and is curved at an angle of approximately thirty (30) degrees.

In FIG. 8, a threaded cannula fitting 333 is attached to the second end 366 of the handpiece 314. The cannula 325 longitudinally extends through an open bore 335 in fitting 333 and into housing cavity 367. Adhesive 337 is used to secure the cannula 325 to the fitting 333. Further, the portion of the cannula 325 which extends from the fitting 333, and thus the handpiece 314, is curved at an angle of approximately thirty degrees (30°).

Figure 9:
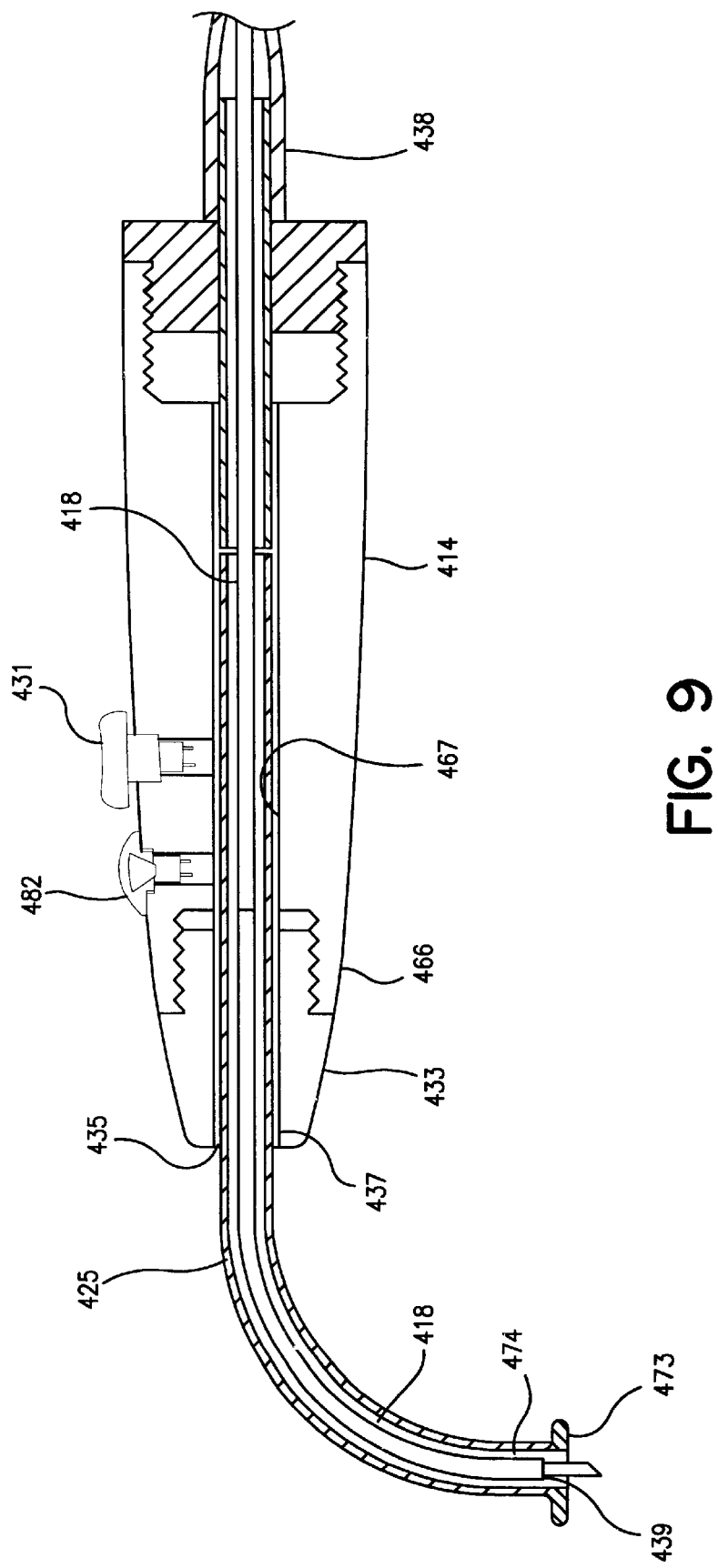
Figure 13:
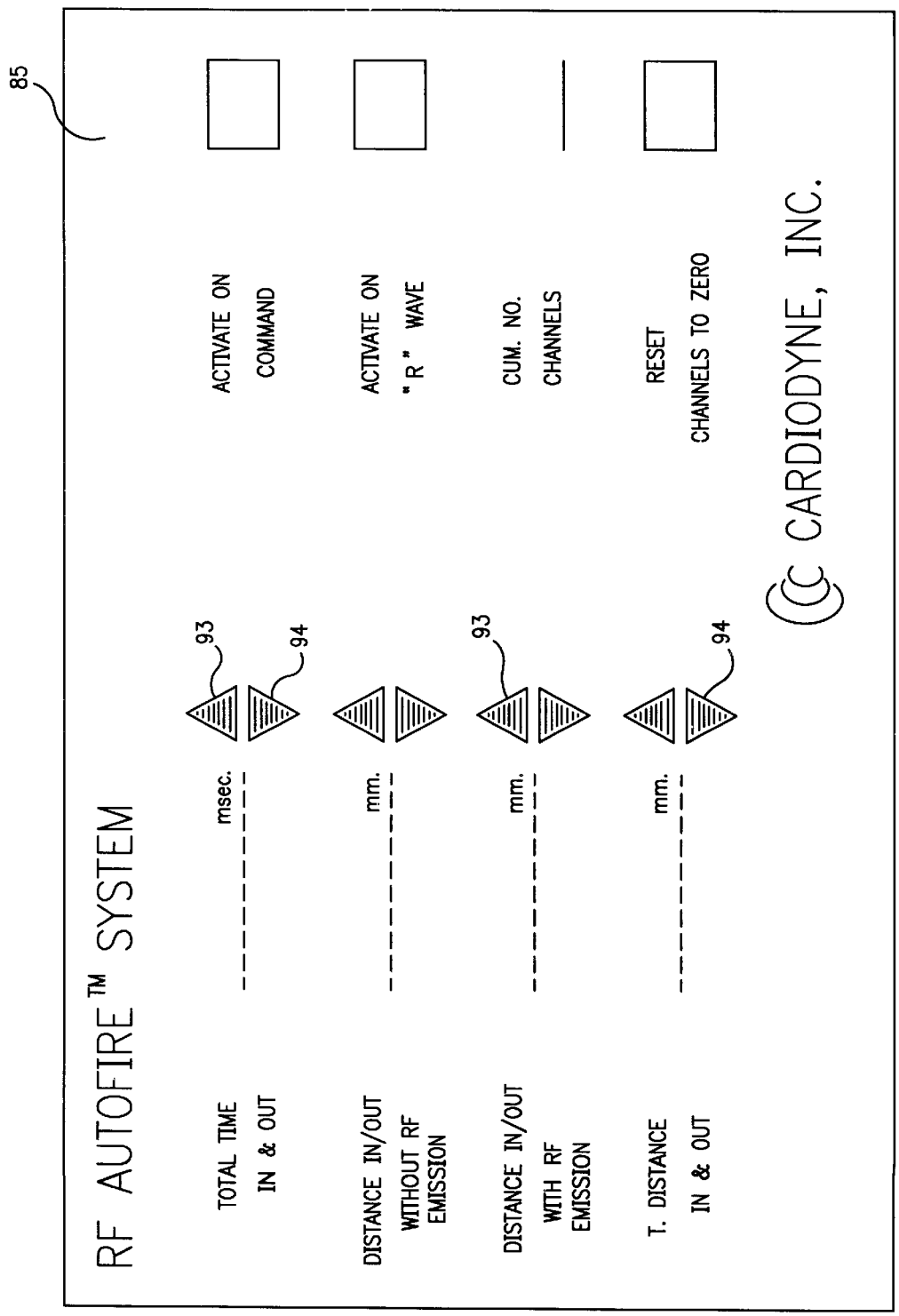
FIG. 13 is a touch-screen display provided by the actuator of FIG. 10.

FIG. 9 illustrates another handpiece 414 which is similar to that shown in FIG. 13, except that the portion of the rigid cannula 425 which extends from the handpiece is bent at an angle of approximately ninety degrees (90°). Alternative shapes of cannula 425 may range from 10° to 180°.

Figure 10:
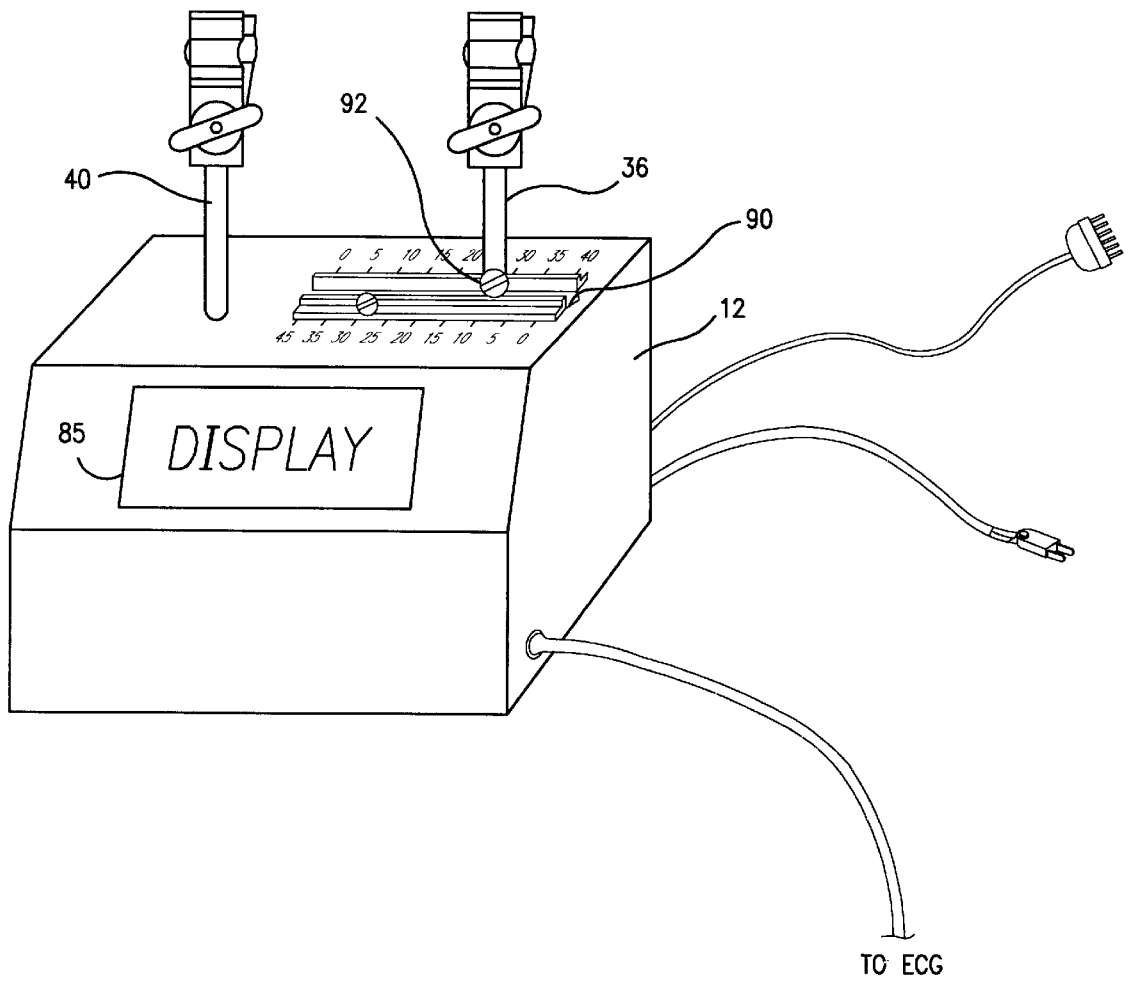
FIG. 10 is a perspective view of the actuator depicted in FIG. 1.
Figure 12:
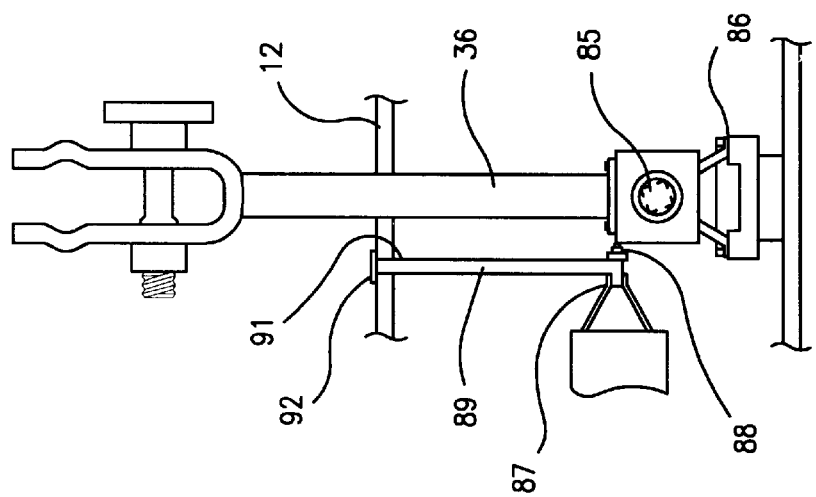
FIG. 12 is an end view of the actuator along plane 12—12 of FIG. 11.
Figure 11:
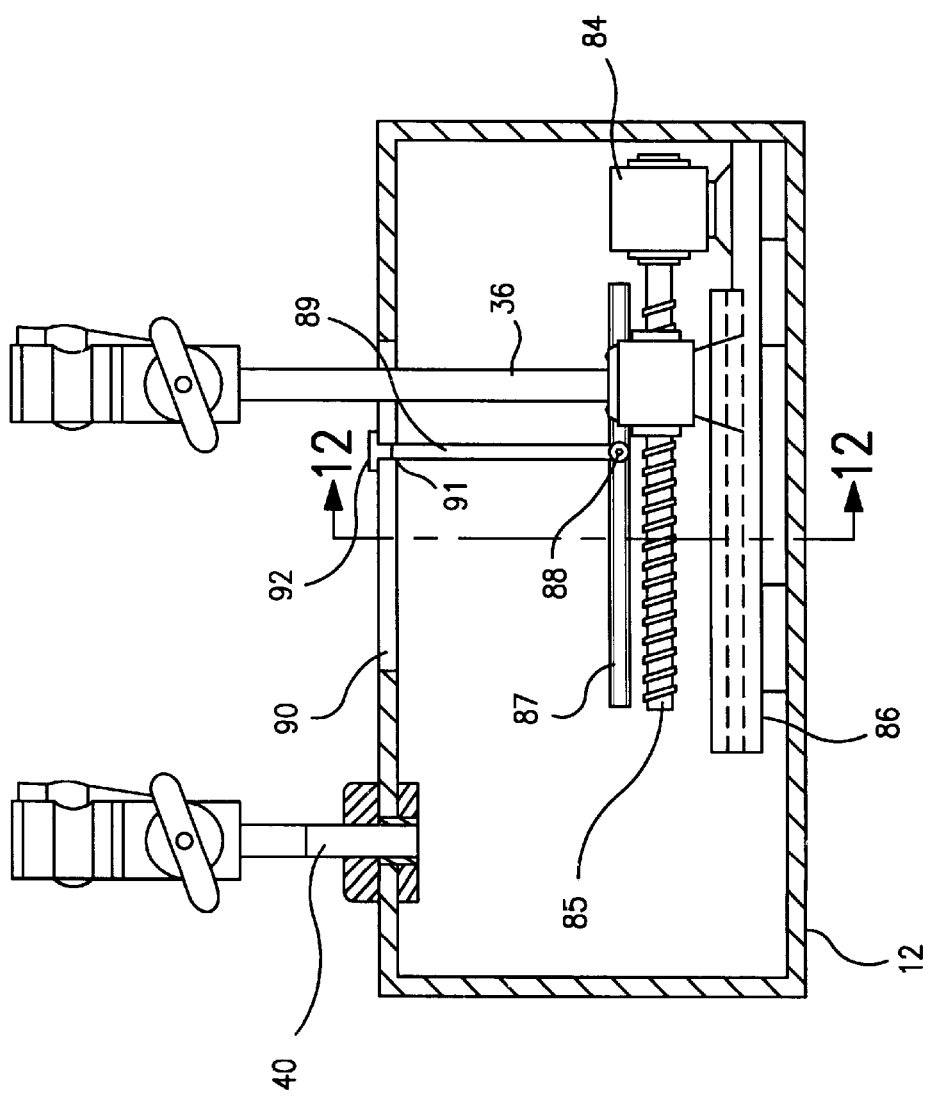
FIG. 11 is a fragmentary partial cross-sectional side view of the actuator of FIG. 10.

FIGS. 10–12 depict the actuator 12 for retracting and advancing the electrical lead assembly 18 into and from, respectively, the bore 74 of cannula 25. The actuator 12 preferably includes a stable speed stepper motor 84 and a conventional active touch-screen display 85. The stepper motor 84 operates to advance and withdraw the electrical lead assembly 18 by moving drive arm 36 towards and away from, respectively, fixed arm 40.

As seen in FIGS. 11 and 12, stepper motor 84 is mounted to the actuator housing and operates to bi-directional rotate shaft 85 which is threadingly engaged by drive arm 36. Also mounted to the actuator housing and in spaced parallel relationship to shaft 85 is track 86 for sliding engaging drive arm 36 between the stepper motor 84 and fixed arm 40.

In operation, longitudinal axial rotation of the shaft 85 by the stepper motor 84 in the clockwise direction, for example, results in the drive arm 36 advancing towards the fixed arm 40. Conversely, rotation in the counterclockwise direction moves the drive arm 36 away from the fixed arm 40.

FIG. 13 depicts a preferred embodiment of the display 85 provided by actuator 12. The display 85 is operably coupled to microcontroller 83 and provides for selection and activation of various functions to be performed by the device 10 during a TMR procedure. The display 85 is activated by conventional means such as the touch of a finger.

The display 85 includes options such as a "ACTIVATE ON COMMAND" touch area for activating the device 10 to form a channel by depressing a footswitch, a button mounted on the handpiece, or a like of switch. The display 85 also includes an "ACTIVATE ON "R" WAVE" touch area to command the device 10 to form a channel after the next recognizable "r" wave of the patient's ECG is received. Further, the display 85 includes a "CUMULATIVE NUMBER OF CHANNELS" area for displaying how many channels have been formed by the device 10. The count shown on the "CUMULATIVE NUMBER OF CHANNELS" area can be reset to zero by touching the "RESET CHANNELS TO ZERO" touch area.

Other operational settings can be included such as the time and distance that the tip 48 of the electrical lead 18 is to advance and retract from the handpiece cannula 25. The above-described settings are selected by up touch area arrows 93 and down touch area arrows 94 provided on the display 85.

Other embodiments can include means for adjusting the amount of time during which the lead 18 is extended through the endocardium into the heart chamber, withdrawn from the endocardium and withdrawn from the epicardium. The above operational settings can also be graphically displayed as overlays on the patent's ECG.

Referring to FIGS. 1, 14A–C and 15, the actuator is enabled by depressing ring 75 or, alternatively, by both depressing ring 75 and the "r" wave of ECG. After partial advancement of the lead assembly into the heart, the RF energy is emitted. Emission of the RF energy can be activated, for example, by the drive arm swiping contact 88 with the actuator 12 as shown in FIGS. 11 and 12.

Also within the external actuator 12 is the controller 83 for determining when to form the channel in heart. The controller 83 makes its determination by interposing an appropriate delay time from the next recognizable "r" wave of the patient's ECG, while taking care to avoid activation in the event of any unusual variations in heart rhythm.

When the controller 83 determines that a channel is to be made, the controller operates stepper motor 84 to advance movable arm 36 towards fixed arm 40. As the arms 36, 40 are moved towards each other, support tube 52 is pushed further within bushing 56 which advances the electrode tip 48 of the lead assembly 18 from the second end 73 of the cannula 25 and into the heart. The lead assembly 18 continues to advance until the lead has traveled the preselected distance entered by the surgeon into the microcontroller 83 by using display 85 as depicted by FIG. 13.

Figure 14A:
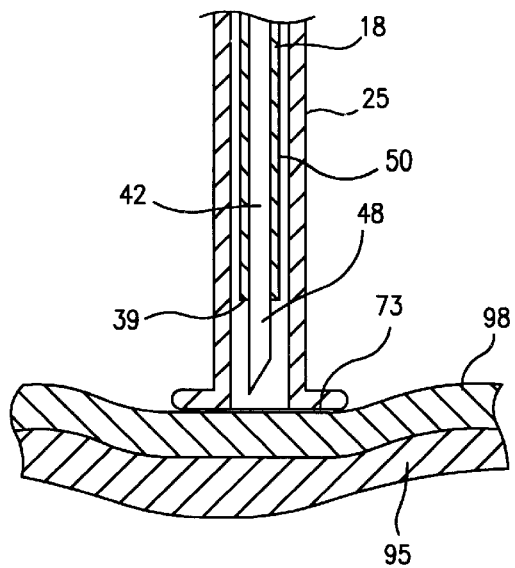
FIG. 14A is a partial cross-sectional view of the cannula extending from the handpiece of FIG. 6 and pressed against the outer surface (epicardium) of a human heart.
Figure 14B:
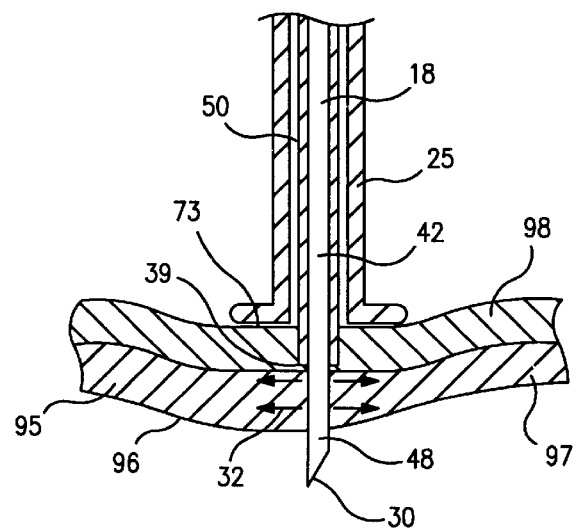
FIG. 14B is a partial cross-sectional view similar to FIG. 14A, but with the lead assembly extending from the handpiece cannula and through the inner layer (endocardium) of the heart.

Preferably, travel of the lead assembly 18 is stopped once the electrode tip 48 punctures through the heart, with the distal end 30 of the lead assembly passing through the inner wall 96 of the heart and into the heart chamber as shown in FIG. 14B. Further, it is desired that the length of the electrode 48 is such that it extends through the endocardium 97 of the heart while the portion of the conductive wire 42 passing through the epicardium 98 of the heart is substantially surrounded by insulation 50 with its terminal end 39 proximate to, or alternatively just within, the endocardium.

Once the advancement of the electrode 48 through the epicardium is completed, the microcontroller 83 enables the RF source 16, via lead 41, to transmit RF energy onto lead 18. This results in current 32 emanating from the electrode 48 to destroy the endocardial tissue 97 about the electrode by producing a high temperature region around the electrode to form inner channel 99a. No RF energy is emitted as lead 18 is withdrawn from the epicardium. The epicardium 98 is not damaged during the emission of RF energy in the endocardium because the insulation 50 between the wire 42 and epicardium prevents the tissue from coming into contact with significant amounts of energy.

The current 32 emanating from the electrode 48 flows back to the RF source 16 by means of the return electrode 24 attached to the patient 26. The transmission of the RF energy from generator 16 is then terminated by the microcontroller 83 and the microcontroller reverses the rotational direction of the stepper motor 84 to retract the electrode tip 48 back into cannula 25. The LED 82 is then turned off by microcontroller 83 to indicated that the channel making process has been completed.

Figure 14C:
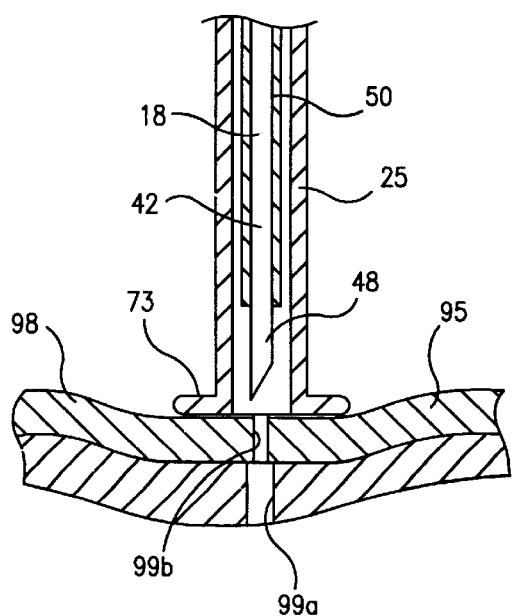
FIG. 14C is a partial cross-sectional view similar to FIG. 14B, but with the lead assembly retracted back into the handpiece cannula after forming a channel in the heart.
Figure 15:
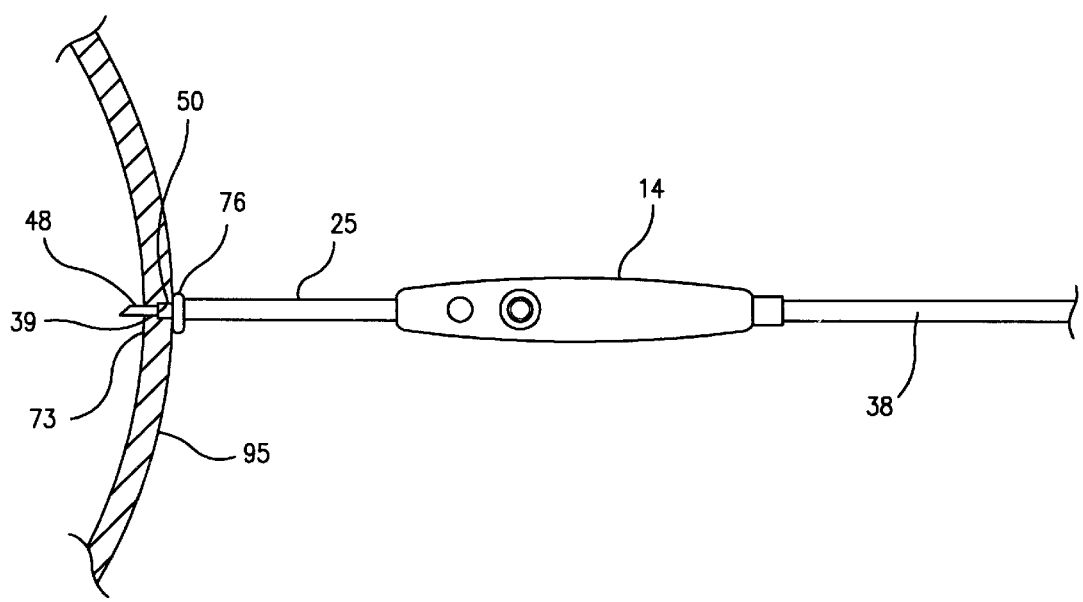
FIG. 15 depicts the cannula of the handpiece of FIG. 1 pressed against a heart wall with the lead assembly puncturing through the heart.

As shown in FIG. 14C, the portion of the channel 99 within the endocardium 97 and indicated by reference number 99a is formed by emission of RF energy. The inner channel 99a allows for blood from the heart chamber to penetrate into the endocardium.

Further, the passage of the unenergized electrode 48 through the epicardium 98 forms a temporary outer channel portion 99b in coaxially alignment and fluid communication with the inner portion 99a. The outer portion 99b has a smaller inner diameter than that of the inner portion 99a. This tapering of the channel 99 into two portions facilitates clotting within the outer portion 99b and thus prevents copious blood loss due to the forceful pumping action of the heart.

Furthermore, the tissue defining the inner wall of the outer channel 99b is relatively undamaged, in contrast to the scorched lining of the inner channel 99a. Thus, unlike the inner channel 99b, the outer channel 99a quickly constricts, clots, and then heals.

After forming the channel 99, the surgeon may reposition the cannula 25 of handpiece 14 to repeat the process of making a channel in the heart 95. As stated above, the RF device can be activated by the button, footswitch or, alternatively, the button and the "r" wave of the patient, depending on whether the heart is arrested or beating.

In an alternative embodiment, the lead assembly of FIGS. 14A–C can be bipolar 118 such as shown in FIG. 3. In such an embodiment, the microcontroller 83 enables the RF source 16 to transmit RF energy to the electrode. However, instead of current emanating from the electrode to destroy endocardial tissue as shown in FIG. 14B, the current path extends through the electrode 148 (i.e., load) and is returned to the RF source 16 via the return lead 122 provided by the bipolar lead assembly 118. In this embodiment, the heat generated from the current passing through the electrode 148 (i.e., load) is sufficient to destroy the endocardial tissue 97 about the electrode 148 to form inner channel 99a.

Figure 16:
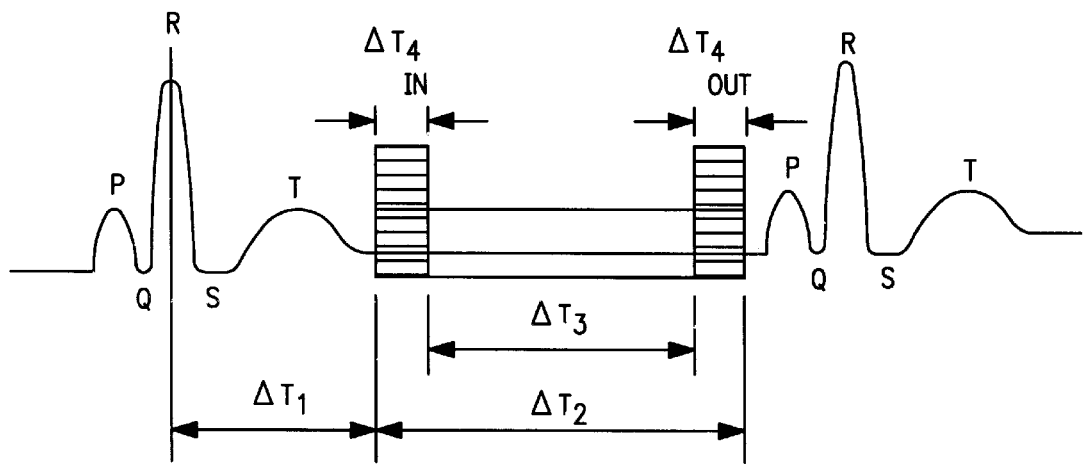
FIG. 16 is an illustrative ECG record with preferred time ranges for performing the various steps to form one channel within a heart with the device of FIG. 1.

Turning to FIG. 16, an illustrative ECG record is depicted with preferred time ranges for performing the various steps required to form one channel within the heart. Preferably, after the peak of the first detected "r" wave, a delay T1 of about 150 milliseconds occurs before the lead assembly 18 is advanced into the heart. Then, the lead assembly is advanced through the epicardium and into the endocardium during T4(IN) which is about 45 to 50 milliseconds.

RF energy is then applied to form a channel during T3. Next, the emission of RF energy is terminated during T4(OUT) which corresponds to the lead assembly being retracted through the epicardium.

Preferably, the time T4(OUT) to retract the lead assembly is substantially equal to T4(IN). Further, the total treatment time T2 is equal to T4(IN)+T4(OUT)+T3 which is in the range of about 300 to 450 milliseconds.

In a further embodiment of the actuator assembly shown in FIGS. 11 and 12, an elongated track 87 may be mounted in the actuator housing for slidingly adjusting the position of sensor 88. The track 87 is generally in spaced parallel relationship to the stepper motor shaft 85. The sensor 88 can be moved along track 87 by attached post 89 which extends into an elongated channel 90 between arms 36 and 40.

Threadably attached to the distal end 91 of post 89 is a set screw 92 for adjustable fixing the position of sensor 88 along track 87. The set screw 92 abuts against the outside of the actuator housing and is adjustably secured to the housing by tightening the set screw. Correspondingly, positioning of the set screw 92 results in like placement of the sensor 88 along track 87.

The sensor 88 can be, for example, operably connected to the RF source 16 for triggering and deactivating the emission of RF energy. Preferably, the sensor 88 is activated, when it first comes in contact with, or is brushed by, drive arm 36. As such, the sensor 88 detects when the drive arm 36 is within a predetermined distance from the fixed arm 40 which corresponds to the distance that the electrical lead assembly 18 is advanced, or retracted, from the outer end 73 of the cannula 25.

When a channel is being made, the stepper motor 84 advances movable arm 36 towards fixed arm 40. Correspondingly, the lead assembly 18 will advance and RF energy will be emitted when movable arm 36 activates switch 88. The energy emission will be stopped as the movable arm 36 retracts the lead assembly 18 and comes in contact with the sensor 88 again to deactivate it.

Referring to FIGS. 17A–17D, another embodiment of the lead assembly is depicted for creating a channel in the inner surface of the heart. The lead assembly 18 is similar to that shown in FIGS. 1–4 except that the length of the mono-polar electrode tip 48' extending from the insulation 50 has been shortened such that the electrode will not enter the heart chamber until after the terminal end 39 of the insulation 50 has also advanced into the endocardium 97.

Figure 17A:
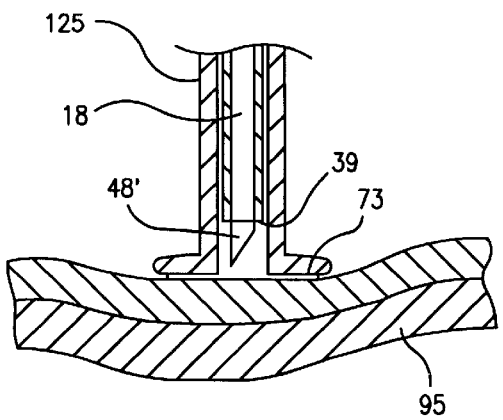
FIG. 17A is a partial cross-sectional view of another embodiment of the lead assembly retracted within the cannula of the handpiece of FIG. 7, that is pressed against the epicardium of a heart.

In FIGS. 17A–17D, the electrical lead 18 is reciprocally mounted within the cannula 25 of the handpiece as described above with regard to FIGS. 1–14. In operation, the second end 73 of the cannula 25 is pressed against the heart 95 as shown in FIG. 17A. The electrode 48' is then advanced from the second end 73 of the cannula 25 into the heart 95.

Figure 17B:
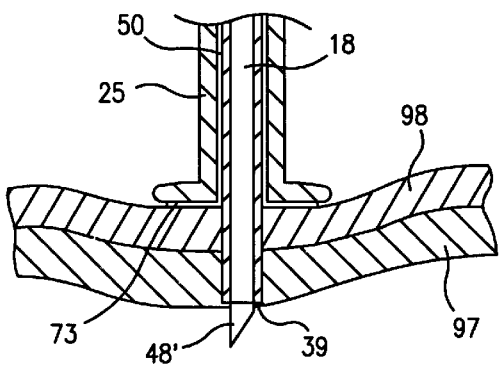
FIG. 17B is similar to FIG. 17A, except that the lead assembly has been extended from the cannula of the handpiece into the epicardium.

Travel of the lead assembly 18 is suspended, preferably, after the electrode 48' penetrates through the heart 95 and partially into the heart chamber by a fixed distance as shown in FIG. 17B. Moreover, a portion of the lead assembly insulating layer 50 extends through the epicardium 98 and into the endocardium 97 of the heart 95.

Figure 17C:
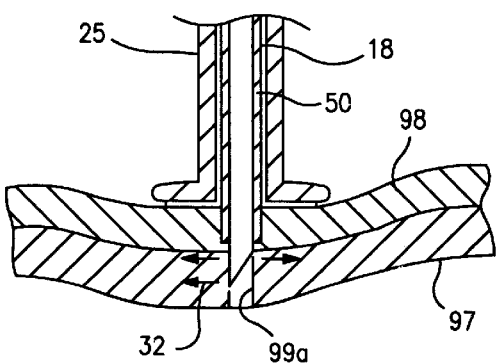
FIG. 17C is a partial cross-sectional view of the lead assembly of FIGS. 17A–17B penetrating through the heart.
Figure 17D:
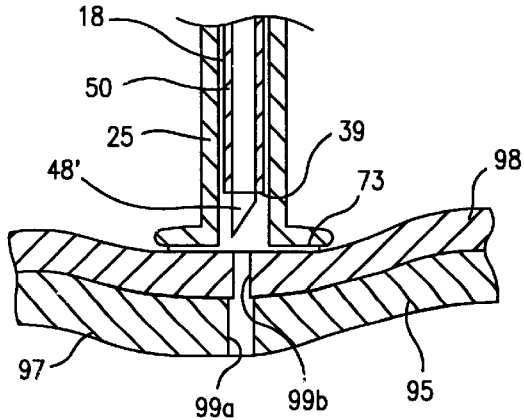
FIG. 17D is a partial cross-sectional view of the lead assembly of FIGS. 17A–17C withdrawn from the heart and into the cannula of the handpiece.

RF energy 32 is then emitted from the electrode 48 to destroy the endocardial tissue 97 about the electrode while the lead assembly 18 is withdrawn from the heart 95. The current 32 continues to emanate from the electrode 48' until, preferably, the terminal end 39 of the lead assembly insulating layer 50 has receded from the endocardium 97 and thus the electrode 48' has just entered the epicardium 98 as shown in FIG. 17C. The unenergized electrode 48' is retracted back into the cannula 25 where the channel 99a formed by transmission of the current extends substantially through the endocardium 97 but, preferably, not into the epicardium 98 as shown in FIG. 17D.

In an alternative embodiment, the lead assembly of FIGS. 17A–D can be bipolar such as that shown in FIG. 3. In such an embodiment, the length of the electrode tip 148 extending from the insulation 150 is shortened so that the bipolar electrode 148 does not enter the heart chamber until after the terminal end 139 of the insulation has also advanced into the endocardium.

In this embodiment, the electrode is advanced into the heart chamber. Then, the RF source transmits RF energy to the electrode 148. However, instead of current emanating from the electrode to destroy endocardial tissue as shown in FIG. 17C, the current path extends through the electrode 148 (i.e., load) and is returned to the RF source 16 via the return lead 122 provided by the bipolar lead assembly 118. In this embodiment, the heat generated from the current passing through the electrode 148 (i.e., load) is sufficient to destroy the endocardial tissue 97 about the electrode 148 to form inner channel 99a.

Preferably, RF energy is transmitted through the electrode 148 (i.e., load) until the terminal end 139 of the lead assembly insulating layer 150 has receded from the endocardium 97 and thus the bipolar electrode has just entered the epicardium 98. The unenergized bipolar electrode is then withdrawn from the heart.

FIGS. 18A–18D depict another embodiment of a lead assembly reciprocally mounted within the cannula of a handpiece for making channels in the inner layer of a heart with RF energy. The lead assembly 518 is like that shown in FIGS. 1, 2, 9–6 and except that it is bipolar, but without using a needle for a load, and includes both the conductive center wire 542 and the return lead 522 in an arrangement similar to that of a coaxial cable. Correspondingly, where appropriate, the last two digits in the 500 series of numerals depicted in FIGS. 18A–18D are connected to elements which have the same function and/or structure as those described with regard to FIGS. 1, 2, 9–6.

The center wire 542 of the lead assembly 518 is coupled to the RF output of the electrosurgical generator 16 of FIG. 1. The distal end 546 of the center wire 542 provides integral electrode 548 with a tip 551 that is pointed, but can have any other desired shape such as, for example, being beveled or blunted.

The center wire 542 is surrounded by an inner electrically insulating layer 517 which is generally tubular in shape and substantially covers the outer surface of the wire length except for electrode 548.

Attached to the outer surface of the inner insulating layer 517 is return lead 522 that surrounds the insulating layer except for a distal portion proximate to electrode 548. The return lead 522 is generally tubular in shape and is made of conductive material such as metal or metal alloy. The return lead 522 may, for example, consists of a single solid conductor or a plurality of braided conductor strands. Desirably, the distal end of the return lead 522 proximate to electrode 548 is inwardly tapered to provide a pointed annular rim 519 adjoining the outer surface of inner insulation layer 517.

The center wire 542 is preferably in longitudinal coaxial alignment with the return lead 522. The inner insulating layer 517 is situated between the center wire 542 and the return lead 522 such that they are electrically isolated from each other. Further, outer electrically insulating layer 550 surrounds the outer surface of the return lead 522 except for proximate to return lead distal end 519 and electrode 548 which projects from the terminal end 539 of the outer insulation.

Figure 18A:
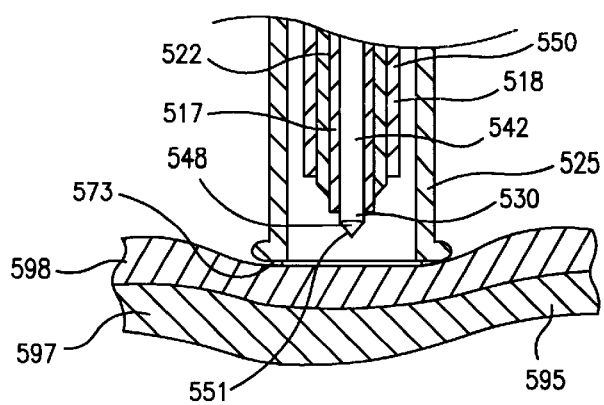
FIG. 18A is a partial cross-sectional view of another embodiment of the lead assembly retracted within a handpiece cannula, similar to FIG. 6, that is pressed against the outer surface of a heart.
Figure 18B:
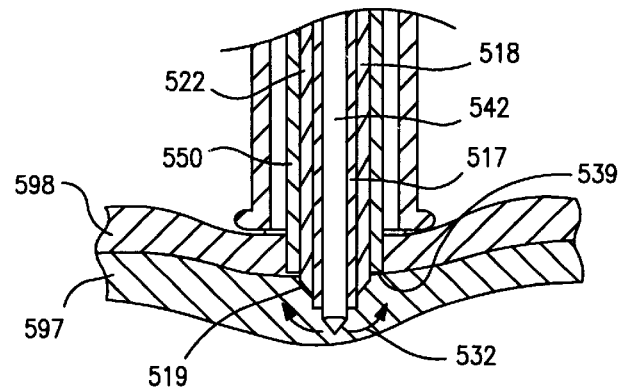
FIG. 18B is a partial cross-sectional view similar to FIG. 18A, but with the lead assembly extending from the handpiece cannula and into the inner (endocardial) layer of the heart.

Turning particularly to FIG. 18A, in operation the second end 573 of the cannula 525 is pressed against heart 595. Next, the lead assembly electrode 548 is advanced from the second end 573 of the cannula 525 and into the heart 595 by the actuator as explained above. The electrode 548 advances through the epicardium 598 and into the endocardium 597 as show by FIG. 18B.

Preferably, the microcontroller activates the RF source to transmit RF energy onto wire 542 once the return lead 522 and the insulation terminal end 539 enter the endocardium 597. Activation of the RF source results in current 532 radiating from the electrode 548 to destroy endocardial tissue 597 and, accordingly, begin burning a channel about the electrode. The current 532 emanating from the electrode 548 flows back to the RF source by entering the tapered end 519 of the return lead 522. Because the return lead 522 and the center wire 542 are not connected to each other via a load such as, for example, the needle 123 of FIG. 3, substantially all current 533 received by return lead 522 must flow through the endocardial tissue 594 between the electrode 548 and return lead tapered end 519. Accordingly, the heat caused by the current flowing through the endocardial tissue 597 results in the destruction thereof.

Figure 18C:
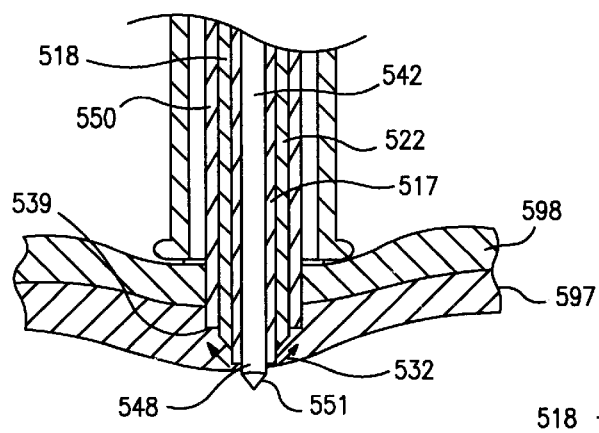
FIG. 18C is a partial cross-sectional view similar to FIG. 18B, but with the lead assembly extending through the heart wall.
Figure 18D:
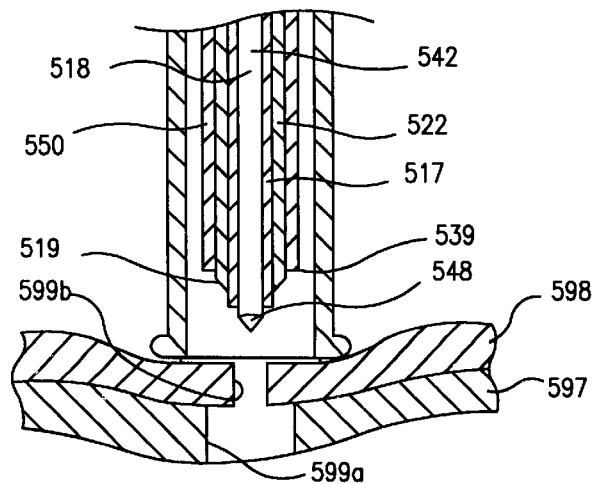
FIG. 18D is a partial cross-sectional view of the lead assembly of FIGS. 18A–C, but with the lead assembly retracted back into the cannula handpiece after forming a channel through the heartwall.

The microcontroller continues to command the actuator to advance the electrode 548 into the endocardium 597 until it is advanced the preselected distance entered by the surgeon using display 85 as depicted in FIG. 13. As the electrode 548 is advanced, current from the RF source is preferably continuously emitted from the electrode. Once the forward travel of the electrode 548 is stopped, the microcontroller reverses the rotational direction of the actuator stepper motor to retract the electrode 548 back into cannula 525. Before the microcontroller begins to retract the electrode, transmission of RF energy may be terminated or, alternatively, the transmission of RF energy may continue until the terminal end 539 of the outer insulation 550 exits the endocardium 597. As depicted in FIG. 18C, the channel 599a in the endocardium 597 formed by destroying the tissue allows blood to enter from the heart chamber.

In an alternative embodiment, the emission of RF energy can be delayed until after the electrode 548 has entered into the heart chamber. Then, RF energy can be emitted from the electrode 548 while the return lead 522 is being withdrawn through the endocardium 597.

In the handpieces previously disclosed and illustrated by FIGS. 1–12, considerable recoil may be encountered when the electrode penetrates the epicardium, which is a tough, very dense, outer layer of the heart muscle. This recoil can be reduced by increasing the rate at which electrode penetrates the epicardium, ramping up to the speed at which the lead penetrates the endocardium. The recoil effect can also be reduced, by allowing the electrode to extend 3 to 6 millimeters from the second end of the cannula. When the second end of the cannula is manually pressed against the heart, the electrode passes into or through the epicardium. When the external actuator is activated, significantly less recoil results as the electrode traverses the remainder of the epicardium and the endocardium.

However, in order to prevent scratching of the heart or other tissue by the exposed electrode when moving the handpiece around the side or posterior surface of the heart, the electrode may be temporarily retracted within the cannula and extended when the handpiece has been re-positioned.

Extending the electrode from the cannula also allows the electrode to cool more effectively in the air, after vaporizing tissue, and avoids heating the second end of the cannula by not enclosing the hot electrode therewithin.

Figure 19:
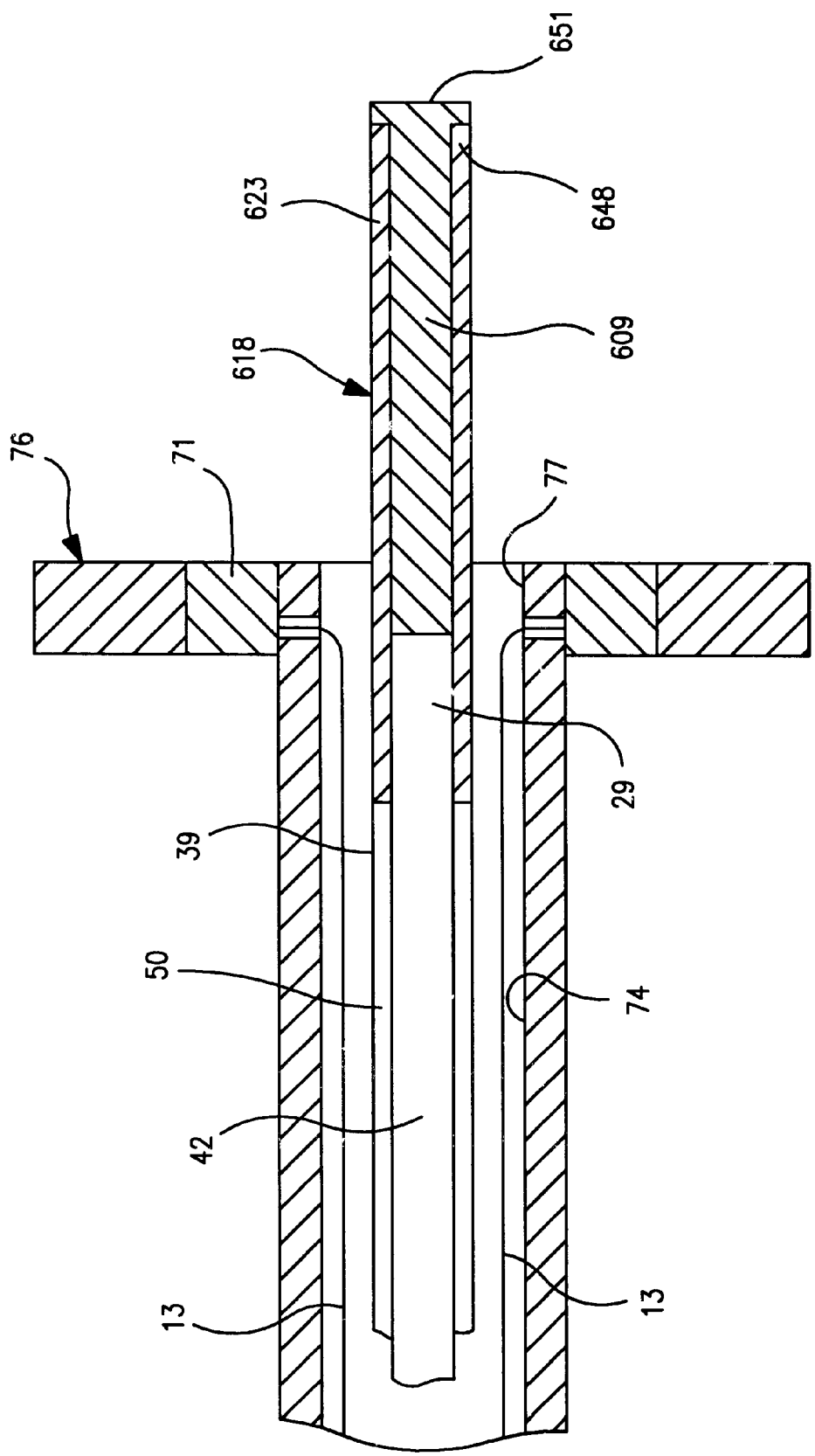
FIG. 19 is an enlarged cross-sectional view of an alternative embodiment of the lead assembly of FIG. 1 extending from the cannula for piezo-electric RF energy delivery.

In an alternative embodiment, piezo-electric sparks can be used to make the channels in the endocardium. In such an embodiment, the device of FIG. 1 is used with a piezo-electric mono-polar electrode such as that shown in FIG. 19. The lead assembly 618 of FIG. 19 is like that shown in FIG. 2 except that, instead of having a pointed tip, the distal end of the electrode 623 is filled with a plug 609 and provides an arcuate planar end 651. Correspondingly, where appropriate, the last two digits in the 600 series of numerals depicted in FIG. 19 are connected to elements which have a similar function and/or structure as those described with regard to FIG. 2.

The plug 609 of FIG. 2 is attached within the bore of tubular teflon electrode 623 and preferably consists of stainless steel or the like. The plug 609 is electrically coupled to conductive wire 42 by conventional means such as, for example, welding. Further, the planar end 651 of the plug 609 preferably has a circumference of about 1.5 millimeters.

Preferably in this embodiment, the electrode 623 is advanced into the heart 95. When the electrode 623 is proximate to the endocardium 97, the RF source 16 energizes the plug 609 which results in current flowing from the plug to the return electrode 24 externally attached to the patient 26. The electrode 623 continues to remain energized while simultaneously being advanced through the heart 95. As the energized plug 609 is advanced, a self producing steam layer isolates the plug from the endocardium tissue 97. Accordingly, sparks jumping between the plug 609 and the endocardium tissue 97 produce very high local energy densities that lead to tissue vaporization.

Once the plug 609 enters the heart chamber, however, the RF source 16 ceases to provide RF energy to the plug 609. The unenergized electrode 609 is then withdrawn from the heart 95.

Referring back to FIG. 1, in an alternative embodiment, the electrode 48 can be exposed before it is inserted into the heart 95. The electrode 48 is manually pushed through the heart 95 and RF energy is emitted from the electrode once it has passed into the heart a preselected fixed distance determined by the surgeon. The activation of the RF energy emission can be enabled and disabled, respectively, for example, by a probe extending from the handpiece. The probe preferably extends parallel to the electrode, but has a shorter length. As such, the electrode extends the preselected fixed distance into the heart when, at about the same time, the distal end of the probe contacts the outer surface of the heart 95. Accordingly, contact of the probe against the heart outer surface enables the emission of RF energy from the electrode.

The probe is preferably spring mounted to the handpiece such that, as the probe continues to advance through the heart, the probe remains pressed against the outer surface. Conversely, the probe preferably is removed from the outer surface of the heart as the electrode is being withdrawn from the heart, which disables the emission of RF energy from the electrode.

In yet another alternative embodiment, the lead assembly can be provided with electromagnetic shielding (not shown) between the insulation layer 50 and the wire 42. The electromagnetic shielding surrounds the wire 42 in an arrangement similar to a coaxial cable. The shielding can consists of conductive material, such as braided copper wires. The shielding is coupled to an electrical ground or the like that is proximate to, or provided by, the RF generator 16. Accordingly, the shielding provides for substantially preventing the radiation of electromagnetic energy from that portion of the lead assembly 18 outfitted with the shielding. Preferably, the electromagnetic shielding extends proximate to the needle 23, but is not in electrical contact therewith.

In Intra-Operative and Endoscopic TMR procedures, in order to make the diameter of the channel larger at the inside surface of the endocardium, (2 to 3 millimeters in diameter as is seen in alligator hearts), the speed at which the electrode advances while emitting RF energy can be varied. If, for example, the heart wall is 15 millimeters thick, after the electrode manually pierces the epicardium to a depth of 4 millimeters, it can be moved by the actuator at a fast rate through the remainder of the epicardium, then begin emitting RF energy while being advanced slower through the 4 to 5 millimeters inner portion of the endocardium and slowest through the last 5 to 6 millimeters of the endocardium.

Conversely, in a Percutaneous TMR procedure, the electrode is contained in a catheter inserted into an artery and extended through the aortic valve into the left ventricle. When the catheter is properly positioned against the chamber wall, which may be accomplished through imaging or electrical sensing means, the channels are made through the endocardium and, optionally, may extend partially into the epicardium.

Figure 20:
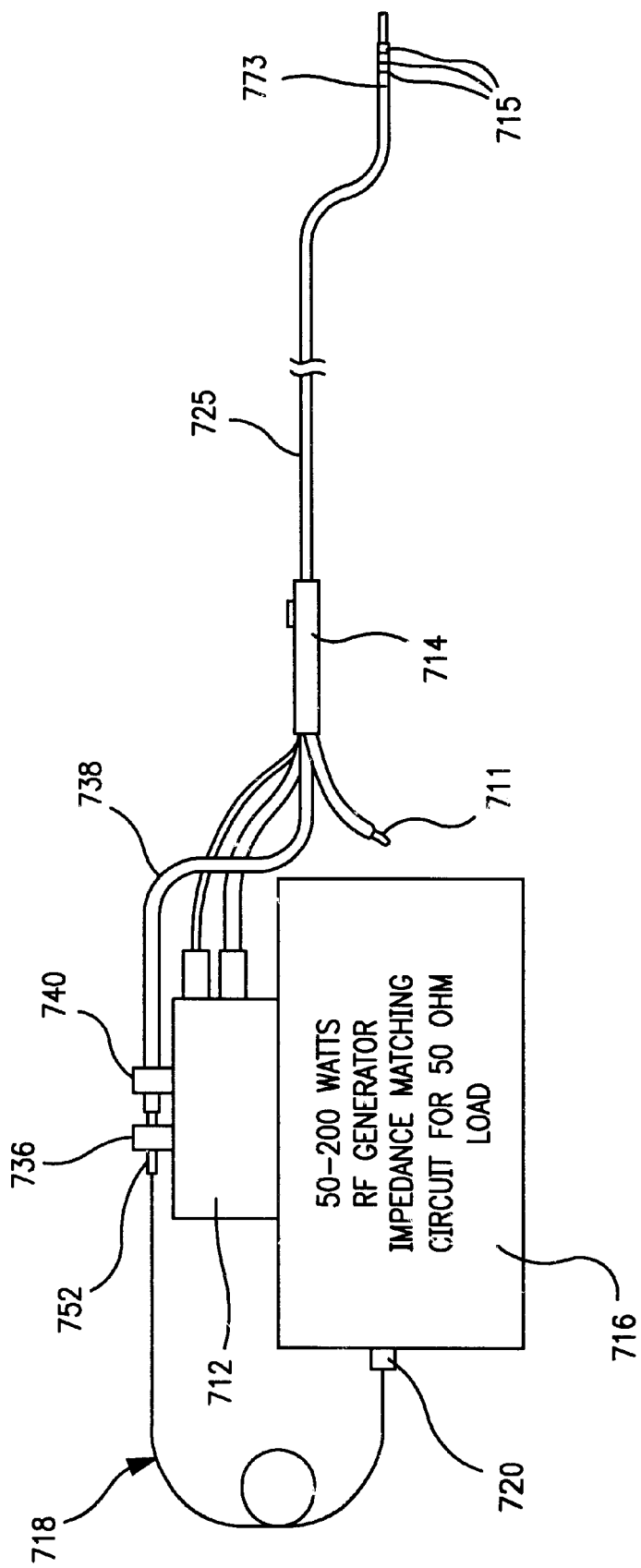
FIG. 20 is a perspective view of another embodiment of the present invention for making channels from the inside of the heart, using a flexible, directable catheter having mapping electrodes.

FIG. 20 is a perspective view of a device for making channels from the inside of the heart. Many of the elements of FIG. 20 are similar to those shown in FIG. 1. Correspondingly, where appropriate, the last two digits in the 700 series of numerals depicted in FIG. 20 are connected to elements which have the same function and/or structure as those described with regard to FIG. 1.

The device 710 includes external actuator 712 which is operably connected to handpiece housing 714 and an RF source 716. Extending from the handpiece is a flexible steerable catheter or cannula 725 that can be inserted into blood vessels or similar bodily areas. The cannula 725 is of conventional construction such that the distal end portion 773 can be navigated through the tortious vascular path to reach the inside of the heart.

Preferably, attached to the cannula distal end portion 773 are serially spaced mapping electrode rings 715 for monitoring parts of the body. Such mapping electrodes are known in the art and, for example, provide for electrically mapping the heart by receiving and transmitting electrical signals related to the operation of that organ to recording signal processing and display devices. Additionally or alternatively, the cannula distal end may be made of a radio-opaque material so that the position of the cannula within the heart chamber can be viewed under fluoroscopy, ultrasound or other imaging techniques.

Turning to FIGS. 21, 22 and 23, coupled to the end of the catheter 725 is a probe assembly 721 that includes a concave tip member or cover 727 having an outer wall that is generally U-shaped in cross-section to form an open catheter attachment end 701 and an opposite outwardly bowed front end 702. Extending from the open end 701 of the tip member 727 is an inner annular shoulder 703 which is received within an outer annular shoulder 704 extending from the distal end 725 of the catheter 725. Further, the circumference of the catheter outer surface is substantially equal to that of the tip member. Thus, a smooth transition is provided from the outer surface of the catheter 725 to the outer surface of the tip member 727.

Extending through the front end 702 of the tip member 727 is an open bore 705 in spaced parallel alignment with the longitudinal axis of the tip member. Attached to the tip member within the bore is a wire anchor 706 and a distal mapping electrode 707.

Coupled to the outer surface of the tip member 727 and surrounding the bore 705 is a ring ultrasound transducer 771. Preferably, the ultrasound transducer 771, anchor 706 and distal mapping electrode 707 have an outer shape wherein the probe assembly 721 has a generally smooth convex outer front surface with a section of bore 705 remaining open to allow for independent reciprocating longitudinal movement of the electrode 748 relative to the tip member 727.

Extending through the catheter are three engagement wires 708 that are spaced at about every 120 degrees about the catheter longitudinal axis as shown in FIG. 21. The engagement wires 708 can be reciprocated within the cylindrical tubing of the catheter 725, the tip member 727, and from apertures generally equally radially spaced on the outer surface of the tip member. The engagement wires 708 preferably are laterally extendable from the apertures in the tip member 727 approximately 2 to 10 millimeters from the tip member's distal end.

When actuated, the engagement wires 708 project from the tip member 727 while uniformly diverging from each other. The distal end portion of each wire 708 are preformed to resiliently bend at an angle such that the wires provide three laterally extending fingers 709 that diverge from each other and anchor the tip member 727 in position by penetrating and engaging the fenestrations attached to the inner surface of the ventricle. Preferably, the wires 708 are made of nitinol. Hooks or wires with barbs can also be used to temporarily anchor the probe tip 727 in place.

Extending within the bore of the catheter 708 are leads 742 for the mapping electrodes 715, 707 and the transducer 771. The leads 742 exit the catheter 725 preferably proximate to the actuator 712 and are attached to a connector 711 for operably coupling the leads to display devices or the like.

Extendable through the catheter 725 and the tip member bore 605 is lead assembly 718. Preferably, the lead assembly 718 is bipolar and is projectable and withdrawable from the front end 702 of the tip member 727.

The distal end 729 of the lead assembly center wire 742 is attached to an electrically conductive needle 723 for providing a generally cylindrical load or electrode 748 with a pointed tip 751. Surrounding the center wire 742 is an inner electrical insulating layer 717 that is generally tubular and covers the outer surface of the wire except at the distal end 729 longitudinally projecting therefrom.

Return lead 722 is coupled to the outer surface of the inner insulating layer 717 and surrounds the insulating layer except for the distal portion proximate to, and extending within, electrode 748. Return lead 722 has generally a tubular shape and consists of a conductive material such as metal or a metal alloy. The return lead 722 can, for example, consists of a single solid conductor or a plurality of braided conductor strands. The distal end of the return lead 722 receives, and is attached thereon, an outer surface portion of the electrode 748 to provide an electrically conductive path therebetween.

Surrounding the outer surface of return lead 722 along its length, except for the portion receiving needle 723, is outer electrically insulating layer 750. The lead assembly 718 extends through hypodermic tube 732 that is mounted within the bore of the catheter 725 and into tip member 727. The hypodermic tube 732 terminates proximate to the inner opening of the tip member bore 705 and is in longitudinal co-axial alignment therewith. The inner wall surface of the hypodermic tube 732 is larger than the outer surface of electrically insulating layer 750 so that the lead assembly can be reciprocated within the hypodermic tube.

Like the other embodiments discussed above, the lead assembly 718 is attached to drive arm 736 of actuator 712 and extends through flexible cannula 738, handpiece 714, and the catheter 725. Further, the lead assembly 718 is allowed to freely reciprocate within the catheter 725, handpiece 714, and cannula 738. Moreover, the flexible cannula 738 is attached to fixed arm 740 of the actuator 712 such that reciprocating movement of the ;drive arm 736, relative to the fixed arm 740, results in like movement of the needle 723 relative to the probe assembly front end 702.

Referring to FIGS. 23A–C, in a procedure using device 710, the probe 721 is positioned against the endocardium 797. The wires 708 are extended from the apertures in the tip member 727 to anchor the tip member in place, relative to the heart's inner wall, by contact with the network strands and fonds that line the heart's inner wall.

The electrode 748 is then advanced distally from the catheter 725 the desired distance, as shown in FIG. 23B, while emitting radio-frequency energy, as described heretofore. The first 6 millimeters of radio-frequency transmission within the heart preferably are at a relatively low rate and the next 4 to 5 millimeters of radio-frequency transmission are at a higher rate, creating a larger diameter channel 790 in the first 6 millimeters of the endocardium.

Next, the emission of RF energy is preferably terminated and the electrode 748 and wires 608 are retract back into the tip member 727 as shown in FIG. 23C.

In alternative embodiments, the electrode 748 of device 710 can have any of the previous embodiments described above such as, for example, the mono-polar electrodes shown in FIGS. 2 and 19. Also, ultrasound or microwave energy may be used with any of the aformetioned embodiments of the invention.

In an embodiment, the positioning of the catheter tip member 727 relative to a beating heart can be accomplished by, for example, the control system disclosed in U.S. Pat. No. 4,788,975, issued to Shturman et al., and incorporated herein by reference. In such a control system, the positioning of the tip member 727, and thus where the channel 790 in the endocardium 797 will be made, is correlated with the movement of the heart 795.

Preferably, a number of image samples of the catheter tip member 727 within the heart are taken at various time periods, by conventional means, during each cardiac cycle. At the cardiac cycle time period that the tip member 727 is positioned at the desired treatment area, the process of forming a channel is executed as described above.

In all of the above disclosed embodiments, ultrasound may be used to assist the surgeon in determining the thickness of the heart wall. The ultrasound image may be displayed on a TV monitor, so that the surgeon can visualize the thickness of the heart wall at the point where the electrical lead penetrates the heart wall. In addition, the penetration of the lead into the heart chamber and steam bubbles, from the emission of radio-frequency energy into the blood in the heart chamber, can be visualized to confirm that the entire heart wall was penetrated.

In another preferred embodiment, the aforesaid ultrasound emitter/receiver may also transmit image data to a microcontroller, such as the one in the actuator, wherein the microcontroller processes the data to determine the thickness of the heart wall. The microcontroller then operates the external actuator such that the lead is advanced to a distance that is equal to the thickness of the heart wall plus a few millimeters to insure complete penetration.

It will be readily apparent from the foregoing detailed description of the invention and from the illustrations thereof that numerous variations and modifications may be effected without departing from the true spirit and scope of the novel concepts or principles of this invention. In addition, microwave, ultrasound, and other forms of energy may be used in similar embodiments to make the channels as described above.

We claim:

1. A method of operating on a patient's heart tissue within a chest cavity, said method comprising:

detecting an "r" wave from a patient's heart, and interposing a delay from the detection prior to penetrating the heart tissue, said heart tissue having an outer epicardium with an outer surface and an inner endocardium with an inner surface at least partly defining a heart chamber;

penetrating said outer surface with an electrical lead extending from a cannula having a through bore, said lead partially surrounded by an electrical insulation material;

advancing said electrical lead a preselected depth into said heart tissue;

transmitting electrical energy through said electrical lead once said electrical lead and said insulation material has reached said preselected depth into said heart tissue;

forming a channel by emitting said electrical energy from said electrical lead as said lead is continually advanced through said heart tissue until said lead penetrates said inner surface, said channel being in communication with said heart chamber and extending back to said preselected depth; and withdrawing said electrical lead from said heart tissue to leave said channel between said heart chamber and said preselected depth such that said channel does not communicate with said outer surface.

2. The method of claim 1 further comprising the step of increasing the rate at which said electrical lead penetrates the heart tissue.

3. The method of claim 1 further comprising the step of increasing the rate at which said electrical lead penetrates the epicardium.

4. The method of claim 1 further comprising the step of forming said channel within one heart beat.

5. The method of claim 1 further comprising the step of stopping said penetration of said electrical lead into said tissue.

6. The method of claim 1 further comprising the step of transmitting a signal to indicate when said electrical lead has penetrated to a desired depth within said heart tissue.

7. The method of claim 1 further comprising:

advancing a housing having a said cannula mounted for reciprocation in said housing towards said heart tissue;

urging said cannula against said heart tissue;

retracting said cannula within said housing; and extending said electrical lead from said cannula.

8. The method of claim 1, wherein the source of energy is microwave.

9. The method of claim 1, wherein the source of energy is ultrasound.

10. The method of claim 1, wherein the source of energy is piezo-electric.

11. The method of claim 1, wherein said patient is a human patient.

12. The method of claim 1, wherein said patient is a mammalian patient.

13. A method for transmyocardial revascularization of a patient's heart, comprising:

detecting an "r" wave from a patient's heart, and timing penetrating of the heart, the heart having an epicardium with an outer surface and an endocardium with an inner surface defining a heart chamber;

penetrating outer surface of said epicardium with an electrical lead extending from a cannula having a through bore, said lead partially surrounded by an electrical insulation material;

advancing said electrical lead into heart tissue to a preselected depth;

initiating radio frequency energy through said electrical lead once said electrical lead and said insulation material has reached said preselected depth;

forming a channel by emitting said radio frequency energy from said electrical lead as said lead is continually advanced into said heart tissue until said lead penetrates said inner surface;

retracting said electrical lead back along said formed channel and from said epicardium; and transmitting said radio frequency energy from said lead while retracting said lead until reaching said preselected depth where said radio frequency energy was initiated.

14. The method of claim 13, wherein said patient is a human patient.

15. The method of claim 13, wherein said patient is a mammalian patient.

16. A method for revascularizing a heart by providing a channel in a heart wall having an outer surface and an inner surface, comprising:

selecting a preferred depth from said outer surface for initiating formation of a channel;

selecting a suitable moment in time for penetrating the heart wall;

penetrating said outer surface with an electrical lead extending from a cannula having a through bore, said lead partially surrounded by an electrical insulation material;

advancing said electrical lead through the heart wall to said preselected depth;

forming a channel by emitting electrical energy from said electrical lead while moving said lead between said preselected depth and said inner surface, said channel being in communication with said heart chamber but terminating proximate to said preselected depth and therefore short of said outer surface; and retracting said electrical lead from said heart wall.

17. The method of claim 16, wherein said channel is formed by emitting said electrical energy in the form of radio frequency energy.

18. The method of claim 17, wherein said step of selecting a suitable time for penetrating said outer surface is determined by an "r" wave emitted from said heart.

19. The method of claim 18, wherein said heart is a mammalian heart.

20. The method of claim 18, wherein said mammalian heart is a human heart located in a chest cavity.

21. The method of claim 18, wherein the method is repeated a plurality of times to form a plurality of channels in said heart wall.

\* \* \* \* \*